US011413311B2

(12) United States Patent
Marom et al.

(10) Patent No.: US 11,413,311 B2
(45) Date of Patent: Aug. 16, 2022

(54) TREATMENT OF MULTIPLE SCLEROSIS WITH LONG ACTING GLATIRAMER AND ADIPOSE-DERIVED STEM CELLS

(71) Applicants: STEM CELL MEDICINE LTD., Jerusalem (IL); MAPI PHARMA LTD., Ness Ziona (IL)

(72) Inventors: Ehud Marom, Tel Aviv (IL); Nadav Bleich Kimelman, Tel Aviv (IL); Frida Grynspan, Mevasseret Zion (IL)

(73) Assignees: MAPI PHARMA LTD., Ness Ziona (IL); STEM CELL MEDICINE LTD., Jerusalem (IL)

( * ) Notice: Subject to any disclaimer, the term of this patent is extended or adjusted under 35 U.S.C. 154(b) by 157 days.

(21) Appl. No.: 16/613,355

(22) PCT Filed: May 15, 2017

(86) PCT No.: PCT/IL2017/050535
§ 371 (c)(1),
(2) Date: Nov. 13, 2019

(87) PCT Pub. No.: WO2018/211486
PCT Pub. Date: Nov. 22, 2018

(65) Prior Publication Data
US 2020/0147141 A1 May 14, 2020

(51) Int. Cl.
*A61K 35/28* (2015.01)
*A61P 25/00* (2006.01)
*A61K 38/02* (2006.01)
*A61K 9/00* (2006.01)

(52) U.S. Cl.
CPC ............. *A61K 35/28* (2013.01); *A61K 38/02* (2013.01); *A61P 25/00* (2018.01); *A61K 9/0019* (2013.01); *A61K 9/0085* (2013.01)

(58) Field of Classification Search
CPC .... A61K 35/28; A61K 9/0019; A61K 9/0085; A61P 25/00
See application file for complete search history.

(56) References Cited

U.S. PATENT DOCUMENTS

| 3,849,550 | A | 11/1974 | Teitelbaum et al. |
| 5,981,589 | A | 11/1999 | Konfino et al. |
| 6,048,898 | A | 4/2000 | Konfino et al. |
| 6,054,430 | A | 4/2000 | Konfino et al. |
| 6,214,791 | B1 | 4/2001 | Arnon et al. |
| 6,342,476 | B1 | 1/2002 | Konfino et al. |
| 6,362,161 | B1 | 3/2002 | Konfino et al. |
| 6,620,847 | B2 | 9/2003 | Konfino et al. |
| 6,844,314 | B2 | 1/2005 | Eisenbach-Schwartz et al. |
| 6,939,539 | B2 | 9/2005 | Konfino et al. |
| 8,008,258 | B2 | 8/2011 | Aharoni et al. |
| 8,021,882 | B2 | 9/2011 | Johnstone et al. |
| 8,216,566 | B2 | 7/2012 | Paludan et al. |
| 8,377,885 | B2 | 2/2013 | Marom et al. |
| 8,404,866 | B2 | 3/2013 | Schwartz et al. |
| 8,642,331 | B2 | 2/2014 | Sadiq et al. |
| 8,679,834 | B2 | 3/2014 | Lombardo et al. |
| 8,703,180 | B1 | 4/2014 | Stankus et al. |
| 8,785,199 | B2 | 7/2014 | Hotta |
| 8,796,226 | B2 | 8/2014 | Marom et al. |
| 9,200,114 | B2 | 12/2015 | Marom et al. |
| 2007/0269413 | A1 | 11/2007 | Serhan et al. |
| 2008/0063687 | A1 | 3/2008 | Chou et al. |
| 2009/0148419 | A1* | 6/2009 | Gonzalez De La Pena ................ A61P 37/06 424/93.7 |
| 2009/0191173 | A1 | 7/2009 | Eisenbach-Schwartz |
| 2009/0291061 | A1 | 11/2009 | Riordan et al. |
| 2011/0008300 | A1 | 1/2011 | Wouters et al. |
| 2011/0129450 | A1 | 6/2011 | Lazarov et al. |
| 2012/0015891 | A1 | 1/2012 | Marom et al. |
| 2012/0064098 | A1 | 3/2012 | Consigny et al. |
| 2012/0164229 | A1 | 6/2012 | Marom |
| 2012/0230966 | A1 | 9/2012 | Crawford et al. |
| 2013/0034524 | A1 | 2/2013 | Agha-Mohammadi |
| 2013/0156725 | A1 | 6/2013 | Marom |
| 2014/0037598 | A1 | 2/2014 | Jansen et al. |
| 2014/0140968 | A1 | 5/2014 | Kadouri et al. |
| 2014/0234272 | A1 | 8/2014 | Vesey et al. |

(Continued)

FOREIGN PATENT DOCUMENTS

| EP | 1592384 B1 | 10/2012 |
| EP | 1827108 B1 | 4/2015 |

(Continued)

OTHER PUBLICATIONS

Ghasemi et al. Transplantation of Human Adipose-Derived Stem Cells Enhances Remyelination in Lysolecithin-Induced Focal Demyelination of Rat Spinal Cord, 2014, Mol Biotechnol 56:470-478 (Year: 2014).*
Choi et al. Cell Proliferation and Neuroblast Differentiation in the Rat Dentate Gyrus After Intrathecal Treatment with Adipose-Derived Mesenchymal Stem Cells 2011 Cell Mol Neurobiol 31:1271-1280 (Year: 2011).*
Ra et al. Stem cell treatment for patients with autoimmune disease by systemic infusion of culture-expanded autologous adipose tissue derived mesenchymal stem cells, 2011 Journal of Translational Medicine 9:181 (Year: 2011).*
Scruggs et al. Age of the Donor Reduces the Ability of Human Adipose-Derived Stem Cells to Alleviate Symptoms in the Experimental Autoimmune Encephalomyelitis Mouse Model Stem Cells Translationalmedicine 2013;2:797-807 (Year: 2013).*

(Continued)

*Primary Examiner* — Taeyoon Kim
*Assistant Examiner* — Alexandra F Connors
(74) *Attorney, Agent, or Firm* — Rothwell, Figg, Ernst & Manbeck, P.C.

(57) ABSTRACT

Methods of treating multiple sclerosis are provided, comprising parenterally administering glatiramer acetate in a sustained-release depot form, and administering adipose-derived stem cells into the central nervous system. According to some aspects the combined treatments provide synergistic effects. In particular the combined therapies offer benefits to progressive forms of multiple sclerosis.

21 Claims, 11 Drawing Sheets

(56) References Cited

U.S. PATENT DOCUMENTS

| | | | |
|---|---|---|---|
| 2014/0308745 | A1 | 10/2014 | Sadiq et al. |
| 2014/0315870 | A1 | 10/2014 | Conget Molina et al. |
| 2015/0030662 | A1 | 1/2015 | Raghunath et al. |
| 2015/0216908 | A1 | 8/2015 | Lee et al. |
| 2017/0065638 | A1 | 3/2017 | Fraser |

FOREIGN PATENT DOCUMENTS

| | | | |
|---|---|---|---|
| JP | 2008521796 A | 6/2008 | |
| JP | 2013516403 A | 5/2013 | |
| JP | 2015511221 A | 4/2015 | |
| JP | 2020519645 A | 7/2020 | |
| WO | 2006057003 A2 | 6/2006 | |
| WO | 2006060779 A2 | 6/2006 | |
| WO | 2010045645 A1 | 4/2010 | |
| WO | 2011080733 A1 | 7/2011 | |
| WO | 2017139795 A1 | 8/2017 | |
| WO | 2018002930 A1 | 1/2018 | |

OTHER PUBLICATIONS

Wolinsky et al. Glatiramer acetate treatment in PPMS: Why males appear to respond favorably Journal of the Neurological Sciences 286 (2009) 92-98 (Year: 2009).*

Martino et al., (2010) Stem cell transplantation in multiple sclerosis: current status and future prospects. Nat Rev Neurol 6(5): 247-255.

Abramsky et al., (1982), Alpha-fetoprotein suppresses experimental allergic encephalomyelitis, J Neuroimmunol, 2(1): 1-7.

Aharoni et al., (2009) Transplanted myogenic progenitor cells express neuronal markers in the CNS and ameliorate disease in experimental autoimmune encephalomyelitis, J Neuroimmunol, 215(1-2): 73-83.

Baer, (2014) Adipose-derived mesenchymal stromal/stem cells: An update on their phenotype in vivo and in vitro, World J Stem Cells, 6(3): 256-265.

Baer and Geiger (2012) Adipose-derived mesenchymal stromal/stem cells: tissue localization, characterization, and heterogeneity, Stem Cells Int, vol. 2012: Article ID 812693; 12 pages.

Ben-Nun et al., (1996) The autoimmune reactivity to myelin oligodendrocyte glycoprotein (MOG) in multiple sclerosis is potentially pathogenic: effect of copolymer 1 on MOG-induced disease, J Neurol., 243(4 Suppl 1): S14-S22.

Bolton et al., (1982) Immunosuppression by cyclosporin A of experimental allergic encephalomyelitis, J Neurol Sci, 56(2-3): 147-153.

Bunnell et al., (2008) Adipose-derived stem cells: isolation, expansion and differentiation, Methods 45(2): 115-120.

Cohen et al., (2007) Randomized, double-blind, dose-comparison study of glatiramer acetate in relapsing-remitting MS, Neurology, 68(12): 939-944.

Constantin et al., (2009) Adipose-derived mesenchymal stem cells ameliorate chronic experimental autoimmune encephalomyelitis, Stem Cells, 27(10): 2624-2635.

Croitoru-Lamoury et al., (2007) Human mesenchymal stem cells constitutively express chemokines and chemokine receptors that can be upregulated by cytokines, IFN-beta, and Copaxone, J Interferon & Cytokine Res, 27(1): 53-64.

Doshi and Chataway (2016) Multiple sclerosis, a treatable disease, Clin Med (Lond), 16(Suppl 6): s53-s59.

Freedman et al., (2010) The therapeutic potential of mesenchymal stem cell transplantation as a treatment for multiple sclerosis: consensus report of the International MSCT Study Group, Mult Scler, 16(4): 503-510.

Johnson et al., (1995) Copolymer 1 reduces relapse rate and improves disability in relapsing-remitting multiple sclerosis.Results of a phase III multicenter, double-blind, placebo-controlled trial, Neurology, 45(7): 1268-1276.

Lin et al., (2012) Is CD34 truly a negative marker for mesenchymal stromal cells?, Cytotherapy 14(10): 1159-1163.

Riordan et al., (2009) Non-expanded adipose stromal vascular fraction cell therapy for multiple sclerosis, J Transl Med, 7: 29; 9 pages.

Sela et al., (1990) Suppressive activity of Cop-1 in EAE and its Relevance to Multiple Sclerosis, Bull Inst Pasteur, 88: 303-314.

Silva and Ferrari; Animal experimental models for understanding and treating Multiple Sclerosis, SMGroup, Dover, DE 19904, USA. Published: Aug. 18, 2016; 16 pages.

Soleimani et al., (2016) Stem Cell Therapy—Approach for Multiple Sclerosis Treatment, Arch Neurosci, 3(1): e21564; 9 pages.

Sorensen et al., (1998) Intravenous immunoglobulin G reduces MRI activity in relapsing multiple sclerosis, Neurology 50(5): 1273-1281.

Stepien et al., (2016) Clinical Application of Autologous Adipose Stem Cells in Patients with Multiple Sclerosis: Preliminary Results, Mediators of Inflamm, vol. 2016: Aritcle ID 5302120; 6 pages.

Teitelbaum et al., (1971) Suppression of experimental allergic encephalomyelitis by a synthetic polypeptide, Eur J Immunol, 1(4): 242-248.

Teitelbaum et al., (1973) Suppression by several synthetic polypeptides of experimental allergic encephalomyelitis induced in guinea pigs and rabbits with bovine and human basic encephalitogen, Eur J Immunol, 3(5): 273-279.

Teitelbaum et al., (1996) Copolymer 1 inhibits chronic relapsing experimental allergic encephalomyelitis induced by proteolipid protein (PLP) peptides in mice and interferes with PLP-specific T cell responses, J Neuroimmunol, 64(2): 209-217.

Traktuev et al., (2008) A population of multipotent CD34-positive adipose stromal cells share pericyte and mesenchymal surface markers, reside in a periendothelial location, and stabilize endothelial networks, Circ Res, 102(1): 77-85.

Zuk et al., (2002) Human adipose tissue is a source of multipotent stem cells, Mol Biol Cell, 13(12): 4279-4295.

ClinicalTrials.gov Identifier: NCT02157064, Outcomes Data of Adipose Stem Cells to Treat Multiple Sclerosis, Sponsor: StemGenex, Retrieved from: https://clinicaltrials.gov/ct2/show/NCT02157064 on Mar. 15, 2017; 3 pages.

Treatment procedure with stem cells. Swiss medica 21, regenerative medicine clinical center, Primary Progresive Multiple Sclerosis—Case 034, Retrieved from: http://www.startstemcells.com/Primary-Progresive-Multiple-Sclerosis-Case034.html on May 8, 2017. 7 pages.

U.S. FDA grants Breakthrough Therapy Designation for Roche's investigational medicine ocrelizumab in primary progressive multiple sclerosis. Investor Update. Basel, Feb. 17, 2016. Retrieved from: https://www.roche.com/investors/updates/inv-update-2016-02-17.htm on Oct. 10, 2019; 5 pages.

Barhum et al., (2009) Intracerebroventricular transplantation of human mesenchymal stem cells induced to secrete neurotrophic factors attenuates clinical symptoms in a mouse model of multiple sclerosis, J Mol Neurosci, 41(1): 129-137.

Devitt et al., (2015) Successful isolation of viable adipose-derived stem cells from human adipose tissue subject to long-term cryopreservation: positive implications for adult stem cell-based therapeutics in patients of advanced age, Stem Cells Int, 2015: 146421; 12 pages.

Hayon et al., (2012) Platelet microparticles promote neural stem cell proliferation, survival and differentiation, J Mol Neurosci, 47(3): 659-665.

Menard et al., (2013) Clinical-grade mesenchymal stromal cells produced under various good manufacturing practice processes differ in their immunomodulatory properties: standardization of immune quality controls, Stem Cells Dev, 22(12): 1789-1801.

Muraro et al., (2017) Long Term Outcomes after Autologous Hematopoietic Stem Cell Transplantation for Multiple Sclerosis. JAMA Neurol. Author manuscript; available in PMC Dec. 27, 2017. 19 pages.

Pisati et al., (2007) Induction of neurotrophin expression via human adult mesenchymal stem cells: implication for cell therapy in neurodegenerative diseases, Cell Transplant, 16(1): 41-55.

Shinmura et al., (2011) Pretreatment of human mesenchymal stem cells with pioglitazone improved efficiency of cardiomyogenic transdifferentiation and cardiac function, Stem Cells, 29(2): 357-366.

(56) References Cited

OTHER PUBLICATIONS

Tsuji et al., (2014) Adipose-derived stem cells: Implications in tissue regeneration, World J Stem Cells, 6(3): 312-321.
Wilkins et al., (2009) Human bone marrow-derived mesenchymal stem cells secrete brain-derived neurotrophic factor which promotes neuronal survival in vitro, Stem Cell Res, 3(1): 63-70.
Azevedo Margarida; "Promising Phase 1 Trial Results of Stem Cell Therapy in Progressive MS Patients Being Presented at AAN Meeting", Multiple Sclerosis News Today Apr. 19, 2016, Retrieved from: https://multiplesclerosisnewstoday.com/news-posts/2016/04/19/promising-phase-1-trial-results-stem-cell-therapy-progressive-ms-patients-presented-aan-meeting/ on Oct. 22, 2019; 6 pages.
Silva Patricia; "Research on Faulty Stem Cells Suggests MS Patients Need Tailored Therapies", Multiple Sclerosis News Today, Apr. 4, 2017, Retrieved from: https://multiplesclerosisnewstoday.com/2017/04/04/study-on-faulty-multiple-sclerosis-stem-cells-suggests-patients-need-tailored-therapies/ on Oct. 22, 2019; 7 pages.
Choudhery et al., (2014) Cryopreservation of whole adipose tissue for future use in regenerative medicine. J Surg Res 187(1): 24-35.
Giacoppo et al., (2017) The transplantation of mesenchymal stem cells derived from unconventional sources: an innovative approach to multiple sclerosis therapy. Arch Immunol Ther Exp (Warsz) 65(5): 363-379.
Gong et al., (2012) Banking human umbilical cord-derived mesenchymal stromal cells for clinical use. Cell Transplant 21(1): 207-216.
Shalaby SM, Sabbah NA, Saber T, Abdel Hamid RA. Adipose-derived mesenchymal stem cells modulate the immune response in chronic experimental autoimmune encephalomyelitis model. IUBMB Life. Feb. 2016;68(2):106-15.
Mirabet V, Alvarez M, Solves P, Ocete D, Gimeno C. Use of liquid nitrogen during storage in a cell and tissue bank: contamination risk and effect on the detectability of potential viral contaminants. Cryobiology. Apr. 2012;64(2): 121-3.
Abcam. (Jan. 10, 2016). Cryopreservation of mammalian cell lines video protocol. https://www.abcam.com/protocols/cryopreservation-of-mammalian-cell-lines-video-protocol.
Bai X, Yan Y, Song YH, Seidensticker M, Rabinovich B, Metzele R, Bankson JA, Vykoukal D, Alt E. Both cultured and freshly isolated adipose tissue-derived stem cells enhance cardiac function after acute myocardial infarction. Eur Heart J. Feb. 2010;31 (4): 489-501.
Zhu M, Heydarkhan-Hagvall S, Hedrick M, Benhaim P, Zuk P. Manual isolation of adipose-derived stem cells from human lipoaspirates. J Vis Exp. Sep. 26, 2013;(79):e50585.

Bonab et al., (2012) Autologous mesenchymal stem cell therapy in progressive multiple sclerosis: an open label study, Curr Stem Cell Res Ther, vol. 7, No. 6, p. 407-414.
Secondary progressive MS (SPMS), National Multiple Sclerosis Society, accessed Jan. 11, 2022, 7 pages.
Primary progressive MS (PPMS), National Multiple Sclerosis Society, accessed Jan. 11, 2022, 7 pages.
Aharoni, "Immunomodulation neuroprotection and remyelination—the fundamental therapeutic effects of glatiramer acetate: A critical review", Journal of Autoimmunity, (2014), 54: 81-92.
Aharoni et al., "Immunomodulatory Therapeutic Effect of Glatiramer Acetate on Several Murine Models of Inflammatory Bowel Disease", the Journal of Pharmacology and Experimental Therapeutics, (2006), vol. 318, No. 1, pp. 68-78.
Boismenu and Chen, "Insights from mouse models of colitis", Journal of Leukocyte Biology, (2000), vol. 67(3): 267-278.
Chinnadurai et al., "Challenges in animal modelling of mesenchymal stromal cell therapy for inflammatory bowel disease", World J Gastroenterol (2015), 21(16): 4779-4787.
Flores et al., "Stem cell therapy in inflammatory bowel disease: A promising therapeutic strategy?", World J Stem Cells, (2015), 7(2): 343-351.
Jung et al., "Human adipose-derived stem cells attenuate inflammatory bowel disease in IL-10 knockout mice", Tissue and Cell, (2015), 47(1): 86-93.
Neuhaus et al., "Pharmacokinetics and pharmacodynamics of the interferon-betas, glatiramer acetate, and mitoxantrone in multiple sclerosis", Journal of the Neurological Sciences, (2007), 259(1-2): 27-37.
Panés et al., "852 Cx601, Expanded Allogeneic Adipose-Derived Mesenchymal Stem Cells (eASC), for Complex Perianal Fistulas in Crohn's Disease: Results From a Phase III Randomized Controlled Trial", Gastroenterology, (2016), 150(4): Supplement 1, p. S181.
Shanahan "Inflammatory bowel disease: immunodiagnostics, immunotherapeutics, and ecotherapeutics", Gastroenterology, (2001),120(3): 622-635.
Han et al., Adipose-Derived Stromal Vascular Fraction Cells: Update on Clinical Utility and Efficacy, Critical Reviews in Eukaryot Gene Expression, 2015, 25(2): 145-152.
Todd et al., "Mesenchymal Stem Cells as Vehicles for Targeted Therapies", In: Drug Discovery and Development—Present and Future edited by Izet M. Kapetanovic, IntechOpen, (2011), DOI: 10.5772/29124, pp. 489-528.

\* cited by examiner

TREATMENT OF MULTIPLE SCLEROSIS WITH LONG ACTING GLATIRAMER AND ADIPOSE-DERIVED STEM CELLS

CROSS-REFERENCE TO RELATED APPLICATIONS

The present application is a national stage filing under 35 U.S.C. § 371 of PCT/IL2017/050535, filed on May 15, 2017. The entirety of the disclosure of the above-referenced application is incorporated herein by reference.

FIELD OF THE INVENTION

The present invention relates to treatment regimens for multiple sclerosis comprising administration of long acting dosage forms of a pharmaceutically acceptable salt of glatiramer and administration of adipose-derived stem cells. In particular, the invention relates to a combined therapy comprising intramuscular or subcutaneous administration of prolonged release forms of glatiramer acetate and intraventricular or intrathecal administration of adipose-derived stem cells.

BACKGROUND OF THE INVENTION

Multiple sclerosis (MS) is a chronic inflammatory disease of the central nervous system (CNS) which typically occurs at young adults, more prevalent in women than in men. MS affects the ability of nerve cells in the brain and spinal cord to communicate with each other and control body functions. The clinical disability is linked to an inflammation of myelin, the protective sheath around the axons of the CNS, which is damaged due to an autoimmune attack and neurodegenerative processes. As a consequence, the white matter of the brain and spinal cord becomes scarred by focal lesions (plaques) leading to neurological dysfunction. There are several patterns of symptoms of MS. Most patients experience a relapsing-remitting (RRMS) course at the initial stage, characterized by unpredictable relapses followed by periods of partial or complete recovery (remission), which at some point becomes progressive (PMS). Such progressive MS is classified as secondary progressive MS (SPMS). Some patients experience a progressive course from the onset of symptoms, and such disease pattern is classified as primary progressive MS (PPMS).

Patients with relapsing-remitting MS are typically treated with corticosteroids during acute attacks (relapses), and with immunomodulatory- or immunosuppressive drugs to prevent new relapses and progression of disability. These include interferon beta (Avonex®, Rebif®, Betaseron®), glatiramer acetate (Copaxone®), dimethyl fumarate (Tecfidera®), fingolimod (Gilenya®) natalizumab (Tysabri®) and the chemotherapeutic agent mitoxantrone in more severe cases. Progressive forms of MS are sometimes treated using similar drugs, but treatment is mainly focused on managing symptoms and rehabilitation. A recent review highlights that progressive MS is an area where there is currently a paucity of available disease-modifying treatments (Doshi and Chataway, 2016, *Clinical Medicine*, 16(6): s53-s59). Ocrelizumab (OCREVUS™) is a humanized anti-CD20 monoclonal antibody, which was granted Breakthrough Therapy Designation for PPMS by the Food and Drug Administration (FDA) in 2016 (Investor Update by Roche, Basel, Feb. 17, 2016).

All treatment options for MS are only partially effective.

Glatiramer Acetate:

Copolymer-1, also known as glatiramer acetate (GA) and marketed under the tradename Copaxone®, is a random polymer (average molecular mass 6.4 kD) composed of the four amino acids L-glutamic acid, L-alanine, L-tyrosine and L-lysine, that are found in myelin basic protein. The average molar fractions of the amino acids are 0.141, 0.427, 0.095 and 0.338, respectively, and the average molecular weight of copolymer-1 is between 4,700 and 11,000 daltons. Chemically, glatiramer acetate is designated L-glutamic acid polymer with L-alanine, L-lysine and L-tyrosine, acetate (salt). Its structural formula is: (Glu, Ala, Lys, Tyr) $xCH_3COOH$ or $(C_5H_9NO_4\_C_3H_7NO_2\_C_6H_{14}N_2O_2\_C_9H_{11}NO_3)xC_2H_4O_2$ [CAS—147245-92-9], approx. ratio $Glu_{14}Ala_{43}Tyr_{10}Lyz_{34}x$ $(CH_3COOH)_{20}$. Copaxone® is a clear, colorless to slightly yellow, sterile, non-pyrogenic solution for subcutaneous injection. Each milliliter contains 20 mg of glatiramer acetate and 40 mg of mannitol. The pH range of the solution is approximately 5.5 to 7.0. Copaxone® is indicated for the treatment of patients with relapsing forms of multiple sclerosis.

The mechanism of action for glatiramer acetate is unknown, although some important immunological properties of this copolymer have emerged. Administration of glatiramer acetate shifts the population of T cells from pro-inflammatory Th1 cells to regulatory Th2 cells that suppress the inflammatory response (FDA Copaxone® label). Given its resemblance to myelin basic protein, glatiramer acetate may also act as a decoy, diverting an autoimmune response against myelin. The integrity of the blood-brain barrier, however, is not appreciably affected by glatiramer acetate, at least not in the early stages of treatment.

Depot Systems of Glatiramer Acetate:

U.S. Pat. No. 8,377,885 discloses long acting parenteral pharmaceutical compositions comprising a therapeutically effective amount of glatiramer and in particular, a composition comprising a therapeutically effective amount of glatiramer acetate in depot form suitable for subcutaneous or intramuscular implantation or injection in treating multiple sclerosis.

U.S. Pat. No. 8,796,226 discloses depot compositions comprising glatiramer acetate and at least one additional drug.

Mesenchymal Stem Cells (MSCs) for the Treatment of Autoimmune and/or Neurodegenerative Diseases:

MSCs are a source of multipotent self-renewing cells, originally identified in adult bone marrow. Naturally, they differentiate to produce osteoblasts, chondrocytes and adipocytes. MSCs provide an accessible source of multipotent stem cells alternative to embryonic stem (ES) cells. MSCs potentially circumvent the need for immunosuppression in cellular therapies since they can be derived from an autologous source and also because they are characterized by an immuno-privileged nature advantageous for allogeneic use.

MSCs based therapies have shown to be effective in preclinical studies for a number of indications including graft versus host disease, stroke, myocardial infarction, pulmonary fibrosis and autoimmune disorders. MSCs are also being extensively researched as a therapeutic tool against neurodegenerative diseases such as Alzheimer's disease (AD), Parkinson's disease (PD), Amyotrophic Lateral Sclerosis (ALS), Huntington's disease (HD) and Multiple Sclerosis (MS). MSCs have been discussed with regard to two aspects in the context of neurodegenerative diseases: their ability to transdifferentiate into neural cells under specific conditions and their neuroprotective and immunomodulatory effects. When transplanted into the brain, MSCs produce neurotrophic and growth factors that protect and induce regeneration of damaged tissue. Additionally, MSCs have also been explored as gene delivery vehicles, for example being genetically engineered to over express glial-derived or brain-derived neurotrophic factor in the brain. Clinical trials involving MSCs are currently underway for MS, ALS, traumatic brain injuries, spinal cord injuries and stroke.

Adipose-Derived Stem Cells (ADSCs):

It has been shown over the past few decades that adipose tissue is in addition to its main function as an energy reservoir also an abundant resource for multipotent stromal cells (Zuk et al., Mol Biol Cell 2002; 13: 4279-4295).

WO 2010/045645 discloses methods of recovering adipose stem cells from adipose tissue.

U.S. Pat. No. 8,021,882 discloses a method for producing stem cell conditioned media for treatment of neurological insults, by providing a culture of adipose stem cells and collecting the supernatants thereof.

Constantin et al. (2009) *Stem Cells.*, 27(10):2624-35 studied intravenous administration of adipose-derived mesenchymal stem cells to mice in chronic experimental autoimmune encephalomyelitis (EAE).

Stepien et al. (2016) *Mediators of Inflammation*, vol. 2016, report a one-year follow-up of MS patients with RRMS or SPMS treated with autologous adipose stem cells injected intrathecally.

WO 2006/057003 discloses, inter alia, methods of stem cell therapy using bone marrow-derived stem cells in combination with glatiramer.

Aharoni et al. (2009) *J Neuroimmunol.*, 215(1-2):73-83 report co-treatment of EAE-induced mice with muscle progenitor cells (MPCs), transplanted either intraventricularly or intraperitonealy, and glatiramer acetate.

There is a need in the art for improved methods for treating multiple sclerosis, particularly for patients with progressive forms of the disease.

SUMMARY OF THE INVENTION

The present invention provides according to some aspects combined therapies for multiple sclerosis (MS) using long acting pharmaceutical compositions comprising a therapeutically effective amount of a pharmaceutically acceptable salt of glatiramer, e.g., glatiramer acetate, and adipose-derived stem cells (ADSCs). In particular embodiments, the present invention provides methods of treating multiple sclerosis comprising parenterally administering glatiramer acetate in a sustained-release depot form, and administering adipose-derived stem cells into the central nervous system.

The present invention is based, in part, on the synergistic effect of the combination of glatiramer acetate in depot form and adipose-derived stem cells on the clinical score in an animal model of multiple sclerosis. The combination was found to be particularly effective in reducing disease score and delaying its onset, and also to significantly slow the progression of the disease. Unexpectedly, a lower dose of the glatiramer acetate depot formulation was found to be more effective when combined with the cells compared to a higher dose. Thus, according to some embodiments, the methods and compositions provided herein allow reducing the glatiramer acetate dose that is given to a patient compared to the dose needed when glatiramer acetate is administered alone.

According to one aspect, the present invention provides a method of treating multiple sclerosis comprising parenterally administering to a subject in need thereof a pharmaceutical composition comprising glatiramer acetate, the pharmaceutical composition being in a sustained release depot form, and administering into the central nervous system (CNS) of the subject human adipose-derived stem cells (hADSCs).

According to another aspect, the present invention provides a pharmaceutical composition comprising glatiramer acetate, the pharmaceutical composition being in a sustained release depot form for parenteral administration, for use in the treatment of multiple sclerosis in combination with human adipose-derived stem cells (hADSCs) administered into the central nervous system (CNS).

According to some embodiments, the pharmaceutical composition comprising glatiramer acetate and the hADSCs are administered on the same day.

According to other embodiments, the pharmaceutical composition comprising glatiramer acetate and the hADSCs are administered on separate days.

According to some embodiments, a period of time between administration of the pharmaceutical composition comprising glatiramer acetate and administration of the hADSCs ranges between 1-14 days. According to additional embodiments, a period of time between administration of the pharmaceutical composition comprising glatiramer acetate and administration of the hADSCs ranges between 1-2 weeks.

According to some embodiments, the pharmaceutical composition comprising glatiramer acetate is administered once every 1-15 weeks. According to additional embodiments, the pharmaceutical composition comprising glatiramer acetate is administered once every 1-10 weeks. According to yet additional embodiments, the pharmaceutical composition comprising glatiramer acetate is administered once every 2-6 weeks. According to some specific embodiments, the pharmaceutical composition comprising glatiramer acetate is administered once every 4 weeks.

According to some embodiments, the hADSCs are administered once.

According to other embodiments, the hADSCs are administered more than once, for example twice, three times, four times, etc. Each possibility represents a separate embodiment of the present invention. According to some embodiments, the hADSCs are administered once every 2-8 months. According to additional embodiments, the hADSCs are administered once every 3-12 months.

According to some embodiments, the pharmaceutical composition comprising glatiramer acetate is administered first, before administration of the hADSCs.

According to other embodiments, the pharmaceutical composition comprising glatiramer acetate is administered second, after administration of the hADSCs.

According to other embodiments, the pharmaceutical composition comprising glatiramer acetate is formulated for subcutaneous implantation, and the administering is via subcutaneous injection.

According to some embodiments, administering the hADSCs is by intrathecal administration.

According to other embodiments, administering the hADSCs is by intraventricular or intracerebroventricular (ICV) administration, namely into the brain ventricles.

According to some embodiments, the hADSCs are derived from human subcutaneous fat obtained by liposuction aspiration.

According to some embodiments, the hADSCs are autologous.

According to other embodiments, the hADSCs are allogeneic.

According to some embodiments, the hADSCs are characterized by positive expression of CD44, CD73 and CD90 by at least 95% of the cells, positive expression of CD105 by at least 90% of the cells, and negative expression of CD45, CD19, CD11B and HLADR by at least 95% of the cells. According to some embodiments, the hADSCs are further characterized by positive expression of CD34 by 0.1-10% of the cells.

According to some embodiments, administering the hADSCs comprises administrating about $10^5$-$3\times10^8$ cells per one administration.

According to some embodiments, the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

According to other embodiments, the glatiramer acetate comprises about 15 to about 100 amino acids.

According to some embodiments, the pharmaceutical composition comprising glatiramer acetate comprises 20 to 500 mg of glatiramer acetate. According to additional embodiments, the pharmaceutical composition comprising glatiramer acetate comprises 20 to 250 mg of glatiramer acetate. According to yet additional embodiments, the pharmaceutical composition comprising glatiramer acetate comprises 20 to 100 mg of glatiramer acetate.

According to some embodiments, the pharmaceutical composition comprising glatiramer acetate comprises a pharmaceutically acceptable biodegradable or non-biodegradable carrier.

According to some embodiments, the carrier is selected from the group consisting of poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, gelatin, collagen, oxidized cellulose, and polyphosphazene. Each possibility represents a separate embodiment of the invention.

According to some embodiments, the pharmaceutical composition comprising glatiramer acetate is in the form of microparticles prepared by a water-in oil-in water double emulsification process.

According to some embodiments, the microparticles comprise an internal aqueous phase comprising a therapeutically effective amount of glatiramer acetate, a water immiscible polymeric phase comprising a carrier selected from a biodegradable and a non-biodegradable polymer, and an external aqueous phase. In some specific embodiments, the water immiscible polymeric phase comprises a biodegradable polymer selected from PLA and PLGA. Each possibility represents a separate embodiment of the invention.

In additional embodiments, the external aqueous phase comprises a surfactant selected from polyvinyl alcohol (PVA), polysorbate, polyethylene oxide-polypropylene oxide block copolymers and cellulose esters. Each possibility represents a separate embodiment of the invention.

The subject to be treated as described herein is typically a human. According to some embodiments, the methods and compositions of the present invention are useful for the treatment of progressive forms of multiple sclerosis (MS). Thus, according to some embodiments, the subject is a subject suffering from a progressive form of MS. In some specific embodiments, the progressive MS is secondary progressive MS. In additional specific embodiments, the progressive MS is primary progressive MS.

These and further aspects and features of the present invention will become apparent from the detailed description, examples and claims which follow.

DETAILED DESCRIPTION OF THE INVENTION

Figure 1:
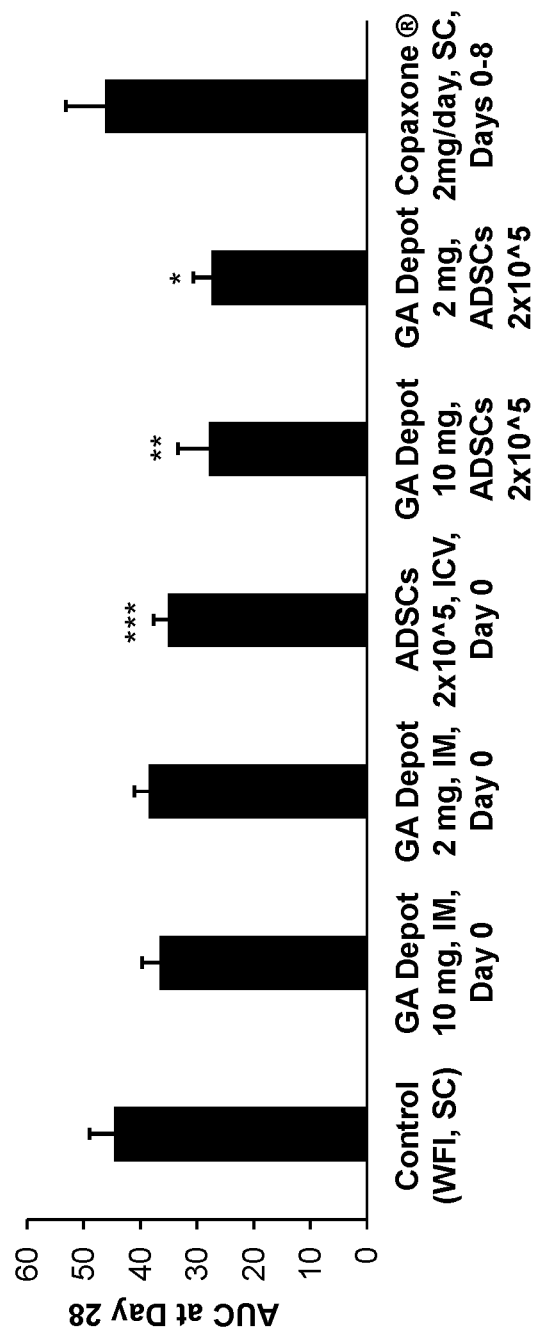
FIG. 1: Effect of GA Depot and ADSCs on EAE as determined by AUC Clinical Score Analysis up to day 28. The agents were administered alone or together at day 0 (GA Depot, 2 mg or 10 mg IM, ADSCs, $2\times10^5$ cells, ICV). WFI and Copaxome® (injected SC) served as controls. *P<0.05 compared with all groups except 10 mg GA Depot and $2\times10^5$ ADSCs;  P<0.05 compared with Copaxone® (2 mg/day) or WFI; * P<0.05 compared with WFI single factor ANOVA followed by one-tail two-sample T test assuming unequal variances, n=10/group, +/−standard error.
Figure 2:
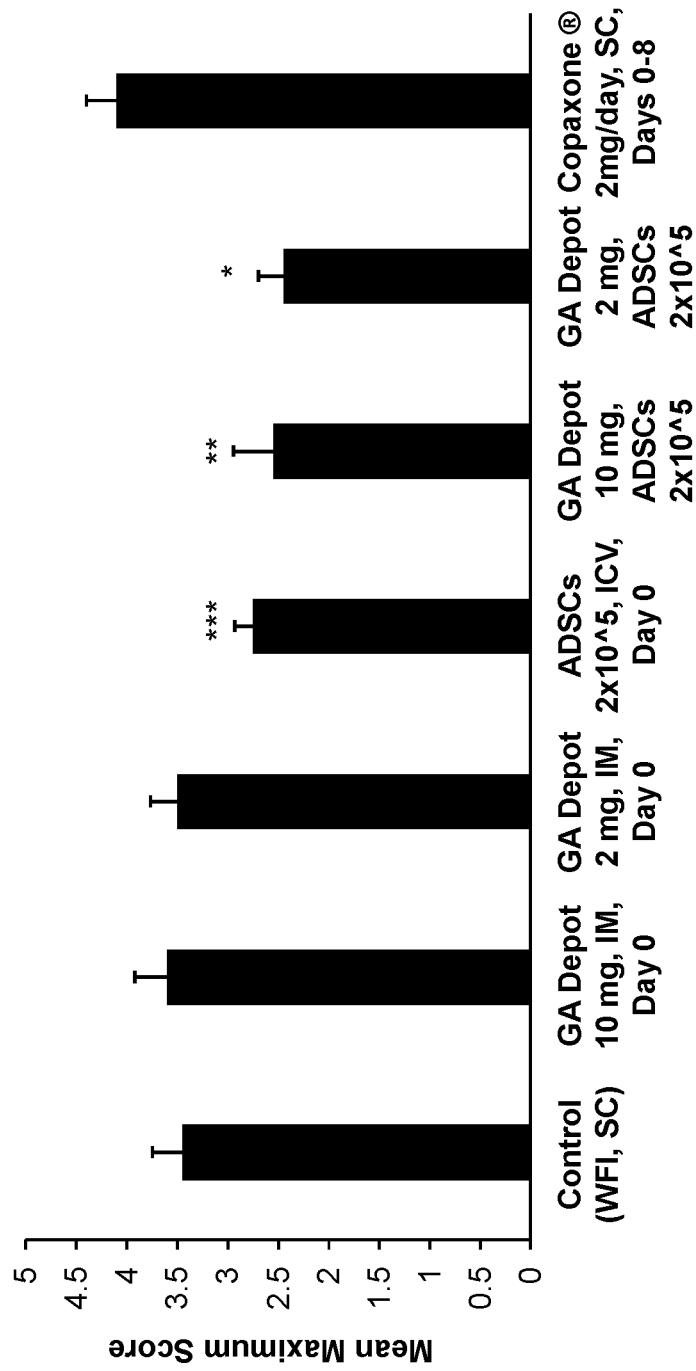
FIG. 2: Effect of GA Depot and ADSCs on EAE as determined by Mean Maximum Score analysis up to day 28. The agents were administered alone or together at day 0 (GA Depot, 2 mg or 10 mg IM, ADSCs, $2\times10^5$ cells, ICV). WFI and Copaxome® (injected SC) served as controls. *P<0.05 compared with all groups except ADSCs and 10 mg GA Depot and $2\times10^5$ ADSCs;  P<0.05 compared with all groups except $2\times10^5$ ADSCs and 2 mg GA Depot and $2\times10^5$ ADSCs; * P<0.05 with all groups except GA, single factor ANOVA followed by one-tail two-sample T test assuming unequal variances, n=10/group, +/−standard error.
Figure 3:
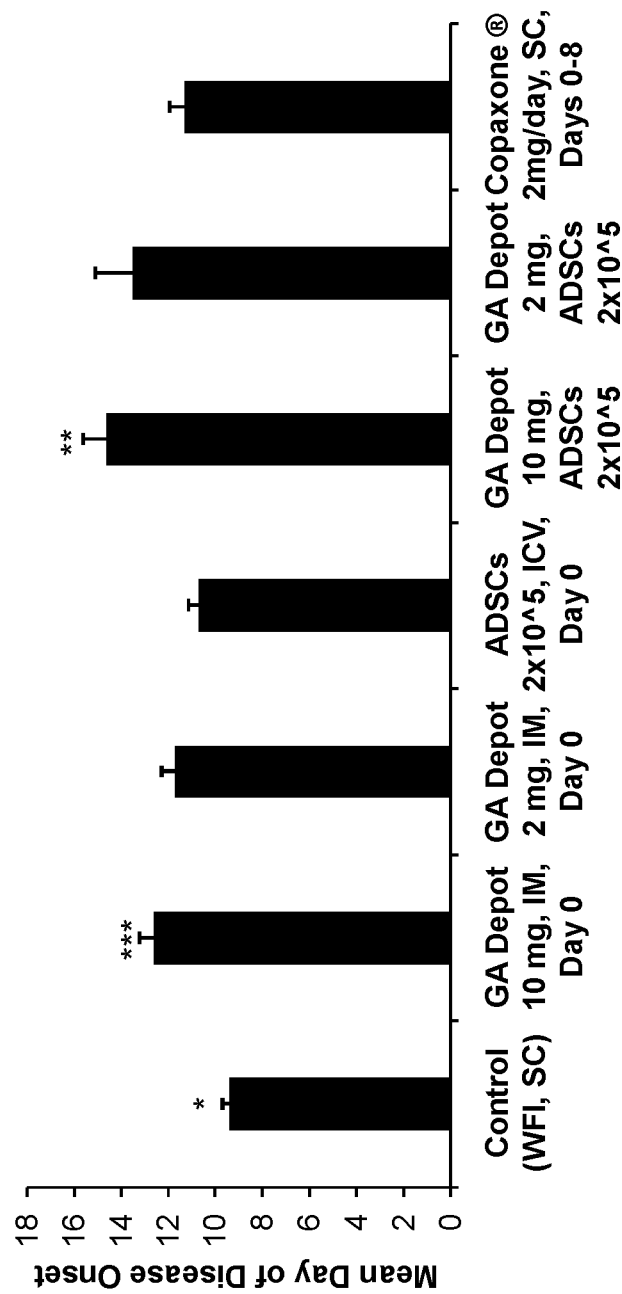
FIG. 3: Effect of GA Depot and ADSCs on EAE as determined by Mean Day of Disease Onset analysis up to day 28. The agents were administered alone or together at day 0 (GA Depot, 2 mg or 10 mg IM, ADSCs, $2\times10^5$ cells, ICV). WFI and Copaxome® (injected SC) served as controls. *P<0.05 compared with all groups;  P<0.05 compared with $2\times10^5$ ADSCs and 2 mg GA Depot; * P<0.05 Compared with $2\times10^5$ ADSCs, single factor ANOVA followed by one-tail two-sample T test assuming unequal variances, n=10/group, +/−standard error.

The present invention provides according to some aspects compositions and methods for treating multiple sclerosis utilizing glatiramer acetate (or any other pharmaceutically acceptable salt of glatiramer) in a long-acting injection formulation combined with adipose-derived stem cells administered into the central nervous system.

Glatiramer acetate long-acting formulation (GA depot) was previously described and evaluated in vitro for analysis of glatiramer acetate release profile, and in vivo using a Myelin Oligodendrocyte Glycoprotein (MOG) induced experimental autoimmune encephalomyelitis (EAE) in mice. In those studies, the GA depot demonstrated equivalent efficacy to Copaxone® in ameliorating EAE symptoms. A 10 mg dose of the GA depot administered once was consistently efficacious in reducing the disease symptoms and in all cases, superior to 2 mg Copaxone® administered daily and to 2 mg GA depot administered once. Additionally, in another set of experiments, similar efficacy of GA depot was noted in a dose range of 4 to 10 mg.

The inventors of the present invention have utilized the MOG induced EAE model for evaluation of the effect of a combined treatment with GA depot and adipose-derived mesenchymal stem cells on the disease outcome. MOG is a glycoprotein believed to be important in the process of myelinization of nerves in the central nervous system (CNS). Immunization with MOG 35-55 peptide is generally used for induction of a chronic EAE in C57BL/6 mice. ADSCs were injected into the brain ventricles (ICV) of mice in which EAE has been induced using MOG. Mice were treated with stem cells alone, GA depot alone or a combination of ADSCs and GA depot 2 or 10 mg.

The surprising observations disclosed for the first time in the present invention, demonstrate a synergistic effect of a combination of GA depot and human ADSCs on EAE, including clinical score, mean day of onset, maximum mean disease score and disease duration.

The present invention thus provides treatment methods and regimens comprising administration of pharmaceutical preparations of pharmaceutically acceptable salts of glatiramer, preferably glatiramer acetate, for sustained release by parenteral administration, and administration of human mesenchymal adipose-derived stem cells. These combined treatments afford superior therapeutic efficacy for multiple sclerosis, to sole treatment with GA or with stem cells. The combined treatment resulted in improved and prolonged effects as determined by various clinical scores.

At present, methods and regiments for treatment of multiple sclerosis, comprising administration of long acting dosage forms of glatiramer acetate and adipose-derived stem cells are not available. Such combined therapies would be beneficial to many patients, particularly to those with advanced disease accompanied by neurological symptoms or physical disabilities. Specifically, this treatment will benefit patients with progressive forms of multiple sclerosis.

The term "treating" as used herein refers to suppression or alleviation of symptoms after the onset of multiple sclerosis. "Treating" also encompasses reducing the rate of progression of the disease, or at least one symptom thereof. Common symptoms after the onset of multiple sclerosis include, but are not limited to, reduced or loss of vision, stumbling and uneven gait, slurred speech, as well as urinary frequency and incontinence. In addition, multiple sclerosis can cause mood changes and depression, muscle spasms and severe paralysis. In particular, the disease is characterized by symptoms such as weakness, numbness, tremor, loss of vision, pain, paralysis, loss of balance, bladder and bowel dysfunction, and cognitive changes (primary symptoms); repeated urinary tract infections, disuse weakness, poor postural alignment and trunk control, muscle imbalance, decreased bone density, shallow, inefficient breathing, and bedsores (secondary symptoms); and depression (tertiary symptoms). In some embodiments, treatment includes: (i) inhibiting the condition, i.e., arresting its development; or (ii) relieving the condition, i.e., causing regression of the condition. Each possibility represents a separate embodiment of the present invention. In some particular embodiments, treating multiple sclerosis according to the present invention comprises slowing disease progression, i.e., slowing the progression of disability.

The "subject" to which the drug is administered is a mammal, preferably, but not limited to, a human. The subject is suffering from multiple sclerosis, namely, diagnosed with multiple sclerosis.

The term "multiple sclerosis" as used herein refers to an auto-immune disease of the central nervous system which is accompanied by one or more of the symptoms described hereinabove. In some embodiments, the MS is relapsing remitting MS. In other embodiments, the MS is a progressive MS. In some embodiments, the progressive MS is secondary progressive MS. In other embodiments, the progressive MS is primary progressive MS. In additional embodiments, the progressive MS is progressive relapsing MS.

According to some embodiments, the glatiramer acetate composition is administered every 2-6 weeks. According to some embodiments, the glatiramer acetate composition is administered every 4 weeks.

According to some embodiments, the ADSCs are administered once. According to some embodiments, the ADSCs are administered multiple times, for example every 2-8 months, every 3-12 months, or less frequent.

According to some embodiments, the ADSCs are administered once and the glatiramer acetate composition is administered once every 2-6 weeks, for example once every 4 weeks.

According to additional embodiments, the ADSCs are administered once every 3-12 months, for example once every 3, 4, 5, 6, 7, 8, 9, 10, 11, 12 months, and the glatiramer acetate composition is administered once every 2-6 weeks, for example once every 4 weeks.

According to additional embodiments, the ADSCs and glatiramer acetate composition are administered according to an alternating schedule.

Adipose-Derived Stem Cells

The present invention utilizes adipose-derived mesenchymal stem cells. As used herein, the terms "adipose-derived mesenchymal stem cells" or "adipose-derived stem cells", abbreviated "ADSCs" or "hADSCs" (i.e., human adipose-derived stem cells), refer to plastic-adherent, multipotent cell population harvested from adipose tissue. The cell population is characterized by positive expression of CD44, CD73 and CD90 by at least 95% of the cells, positive expression of CD105 by at least 90% of the cells, and negative expression of CD45, CD19, CD and HLADR by at least 95% of the cells.

In some embodiments, the cell population is characterized by positive expression of CD44, CD73 and CD90 by at least 98% of the cells, positive expression of CD105 by at least 90% of the cells, and negative expression of CD45, CD19, CD11B and HLADR by at least 98% of the cells.

The cell population is further characterized by positive expression of CD34 by up to 10%-20% of the cells. In some embodiments, the cell population is characterized by positive expression of CD34 by up to 5%, 6%, 7%, 8%, 9% or 10% of the cells. Each possibility represents a separate embodiment of the present invention.

In some embodiments, at least 50% of the cells are positive for CD105, CD73, CD44 and CD90, and negative for CD45, CD19, CD11B and HLADR.

According to some embodiments, 90-100% of the human ADSCs are positive for the markers: CD44, CD73 and CD90. According to additional embodiments, at least 95% of the human ADSCs are positive for the markers: CD44, CD73 and CD90. According to yet additional embodiments, at least 98% of the human ADSCs are positive for the markers: CD44, CD73 and CD90.

According to some embodiments, 65-100% of the human ADSCs are positive for CD105. According to additional embodiments, 80-100% of the hADSCs are positive for CD105. According to yet additional embodiments, 90-100% of the hADSCs are positive for CD105. According to yet additional embodiments, 80-95% of the hADSCs are positive for CD105.

According to some embodiments, 0.1-20% of the human ADSCs express the marker CD34. According to additional embodiments, 0.1-10% of the human ADSCs express the marker CD34. According to yet additional embodiments, 0.1-5% of the human ADSCs express the marker CD34. According to yet additional embodiments, 0.5-2% of the human ADSCs express the marker CD34

According to other embodiments, 2-10% of the hADSCs are positive for the marker CD34. According to other embodiments, 2-5% of the hADSCs are positive for the marker CD34. According to some embodiments, at least 90% of the cells, for example at least 95% of the cells, are negative for the marker CD34.

According to some embodiments, at least 90% of the administered human ADSCs are negative for the markers: CD45, CD19, CD11B and HLADR. According to additional embodiments, at least 95% of the administered human ADSCs are negative for the markers: CD45, CD19, CD11B and HLADR. According to yet additional embodiments, at least 98% of the administered human ADSCs are negative for the markers: CD45, CD19, CD11B and HLADR.

According to some embodiments, at least 50% of the injected human ADSCs are positive for CD105, CD73, CD44 and CD90, and negative for CD45, CD19, CD11B, and HLADR. According to additional embodiments, at least 60%, 70%, 80% or 90% of the injected human ADSCs are positive for CD105, CD73, CD44 and CD90, and negative for CD45, CD19, CD11B and HLADR. Each possibility represents a separate embodiment of the invention.

Characterization of cell surface marker expression can be performed by methods known in the art, for example using fluorescence-activated cell sorting (FACS). FACS protocols are reviewed, for example, in: Flow Cytometry Protocols, Methods in Molecular Biology Volume 699 2011, Editors: Teresa S. Hawley, Robert G. Hawley Humana Press. Exemplary procedures are described below.

Adipose tissue as a source for multipotent stromal/stem cells has several advantages over other sources (Baer P C, Geiger H. *Stem Cells Int* 2012; 2012: 812693). For example, subcutaneous fat is omnipresent in humans and is easily accessible in large quantities by liposuction aspiration. Liposuction is a well-tolerated procedure yielding large quantities of tissue aspirate. The lipoaspirate is typically discarded as medical waste, qualifying it as a good starting material for adipose-derived stromal/stem cell (ASC) isolation. The tissue contains a large number of multipotent cells which can be isolated and proliferated in culture.

According to some embodiments, the ADSCs are derived from human subcutaneous fat. According to particular embodiments, the cells are derived from human subcutaneous fat obtained by liposuction aspiration. The ADSCs may be obtained by liposuction procedures in various areas of the body including stomach, hips, thighs, arms, neck and buttocks. Any procedure of liposuction may be used according to the present invention for obtaining ADSCs, including but not limited to laser, ultrasound and fat removal by abdominoplasty, as known in the art.

The adipose tissue is processed to isolate the adipose-derived stem cells, for example according to the procedure described in Example 1 below. Preparation methods typically include steps of washing the tissue with buffers such as PBS and saline, and/or with growth media such as DMEM, StemMACS™ or Plasma-Lyte, and treating the tissue with a tissue-dissociation enzyme such as collagenase and/or subjecting the tissue to mechanical agitation/disruption. Digestion of the sample can also be performed using a combination of dispase and collagenase. Liposomes, which are generally aggregated, can be separated from free stromal cells which include the stem cells and other cells such as red blood cells endothelial cells, and fibroblast cells, by centrifugation. Erythrocytes can be lysed from the suspended pellet using a suitable lysis buffer and the remaining cells can be filtered or centrifuged.

Optionally, cells may be separated by cell sorting or separated immunohistochemically. Bunnell et al. (2008) *Methods.*, 45(2): 115-120, review methods for isolation of ADSCs.

In some preferred embodiments, the ADSCs are cultured before being provided to a subject in need thereof (or before being stored for later use). Preferably, the cells are cultured in a xeno-free medium. In some embodiments, the ADSCs are grown to about 80-100% confluency, for example to about 80% confluency, and sub-cultured to a passage number between 3-10, preferably between 3-5, or 3-4, before administration to the subject. Thus, in some embodiments, the administered cells are at a passage between 3 to 5. In some embodiments, the ADSCs are sub-cultured to passage number 3. In some embodiments, the ADSCs are sub-cultured to passage number 4. In some embodiments, the ADSCs are sub-cultured to passage number 5.

Before administration, cells are counted and prepared for injection in a pharmaceutically acceptable diluent/carrier. Typically, the cells are concentrated before administration to the subject. The concentration typically ranges from $1.6 \times 10^4$/ml to $100 \times 10^6$/ml.

A stem cell composition for single administration according to the methods of the present invention comprises, in some embodiments, $10^5$-$3 \times 10^8$ human ADSCs. According to some embodiments, the composition comprises $10^5$-$10^8$ human ADSCs. According to additional embodiments, $10^6$-$10^7$ human ADSCs are injected in one administration.

According to yet additional embodiments, $200 \times 10^6$-$300 \times 10^6$ human ADSCs are injected in one administration. According to yet additional embodiments, $10^7$-$2 \times 10^8$ human ADSCs are injected in one administration.

According to some embodiments, the ADSC composition of the present invention is for use by systemic administration. Typically, the administration is into the central nervous system (CNS) of a subject. Such administration may be aimed at bypassing the blood brain barrier. According to yet other embodiments, the ADSCs are administered directly to a specific region of the brain.

According to some embodiments the composition is administered to the CNS, for example by intraspinal administration. According to some embodiments, the composition is administered intrathecally. According to other embodiments, the composition is administered by intraventricular or intracerebroventricular (ICV) route, namely into the brain ventricles.

Intraventricular drug delivery is the delivery of medication within the cerebrospinal fluid of the cistern (C1-2 vertebra) and intracranial ventricles. By administering medication directly, less medication is needed, and fewer side effects are seen than with orally administered drugs. The medicine is typically delivered through an implanted catheter connected to a pump, as known in the art. The pump may be programmable, and either implanted or external.

Intrathecal administration is a route of administration for drugs via an injection into the spinal canal, more specifically into the subarachnoid space so that it reaches the cerebrospinal fluid (CSF) and is useful in spinal anaesthesia, chemotherapy, or pain management applications. This route is also used to introduce drugs that fight certain infections, particularly post-neurosurgical. The drug needs to be given this way to avoid the blood brain barrier. Intrathecal and epidural drug delivery comprise the intraspinal routes of drug administration. Each route delivers drug to the cerebrospinal fluid (CSF). Intrathecal delivery involves the direct injection of the drug into the CSF within the intrathecal space of the spinal column, whereas drugs injected in the epidural space have to cross the dura membrane in order to reach the CSF. As such, epidurally administered drugs can also reach the systemic circulation whereas intrathecally administered drugs are confined within the CSF circulating in the spinal column and the brain ventricles.

Glatiramer Formulations

The term "glatiramer acetate" as used herein refers to a compound formerly known as Copolymer 1 that is sold under the trade name Copaxone® and consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate in Copaxone® is 4,700-11,000 daltons (FDA Copaxone® label) and the number of amino acid ranges between about 15 to about 100 amino acids. The term also refers to chemical derivatives and analogues of the compound. Typically the compound is prepared and characterized as specified in any of U.S. Pat. Nos. 5,981,589; 6,054,430; 6,342,476; 6,362,161; 6,620,847; and 6,939,539, the contents of each of these references are hereby incorporated in their entirety.

The term "parenteral" as used herein refers to routes selected from subcutaneous (SC), intravenous (IV), intramuscular (IM), intradermal intraperitoneal (IP) and the like. Each possibility represents a separate embodiment of the invention.

In some embodiments, the glatiramer formulation is administered by intramuscular, subcutaneous, percutaneous, intravenous, or inhalation administration. Each possibility represents a separate embodiment of the invention. According to certain specific embodiments, the glatiramer formulation is for subcutaneous or intramuscular implantation.

The term "therapeutically effective amount" as used herein is intended to qualify the amount of glatiramer that will achieve the goal of alleviation of the symptoms of multiple sclerosis, or at least one of the symptoms of the disease. Suitable doses include, but are not limited to, 20-750 mg for each dosage form. However, it is understood that the amount of glatiramer administered will be determined by a physician, according to various parameters including the chosen route of administration, the age, weight, and the severity of the patient's symptoms. According to various embodiments of the present invention, the therapeutically effective amount of glatiramer ranges from about 1 mg to about 500 mg/day. Alternatively, such therapeutically effective amounts of glatiramer are from about 20 mg to about 100 mg/day.

The term "long acting" as used herein refers to a composition which provides prolonged, sustained or extended release of the glatiramer salt to the general systemic circulation of a subject or to local sites of action in a subject. This term may further refer to a composition which provides prolonged, sustained or extended duration of action (pharmacokinetics) of the glatiramer salt in a subject. Such compositions are also referred to herein as a "sustained release depot form". In particular embodiments, the long acting pharmaceutical compositions of the present invention provide a dosing regimen which ranges from once weekly to once every 6 months. It releases a therapeutically effective amount of the pharmaceutically acceptable salt of glatiramer over a period of about one week to about 6 months. According to currently more preferable embodiments, the dosing regimen ranges from once a week, twice monthly (approximately once in every 2 weeks) to once monthly. Depending on the duration of action required, the depot formulation will typically contain between about 20 and 750 mg of the active ingredient, designed to be released over a period ranging from a couple of weeks to a number of months.

In certain embodiments, the glatiramer formulation is administered in a concentration of 20-30 mg GA per 1 mL of a carrier. In certain embodiments, the carrier is water for injection (WFI). The term "water for injection" or "WFI" as used herein generally means sterile, pure water that meets regulatory standards for e.g. particulates, dissolved solids, organics, inorganics, microbial and endotoxin contaminants. In certain embodiments, the glatiramer formulation is administered in WFI or a buffer containing a suspending agent (e.g. carboxymethylcellulose, CMC), a buffering agent (e.g. citrate salts) and/or a tonicity agent (e.g. NaCl).

In certain embodiments, the glatiramer formulation comprises 10% to 40% solids. In additional embodiments, the glatiramer formulation comprises 20% to 30% solids. In certain embodiments, the glatiramer formulation comprises a Poly(Lactide-co-Glycolide) (PLGA) copolymer. In certain embodiments, the PLGA copolymer is a poly(D,L-lactide-co-glycolide) (50:50) copolymer. In some embodiments, the glatiramer formulation comprises 150-1500 mg PLGA copolymer per 40 mg of GA. In some specific embodiments, the glatiramer formulation comprises 550 mg PLGA copolymer per 40 mg of GA. In certain embodiments, the PLGA copolymer at least partly encapsulates the GA. In certain embodiments, the PLGA copolymer encapsulates the GA.

In certain embodiments, less than 30% of the GA is released from the depot formulation within 7 days in PBS at 37° C. under continuous agitation. In certain embodiments, more than 20% of the GA is released from the depot formulation within 7.5 days in PBS at 37° C. under continuous agitation. In certain embodiments, less than 45% of the GA is released from the depot formulation within 14 days in PBS at 37° C. under continuous agitation. In certain embodiments, more than 90% of the GA is released from the depot formulation within 28 days in PBS at 37° C. under continuous agitation.

In some embodiments, the depot formulations used in the methods of the present invention include, but are not limited to, suspensions of glatiramer or a pharmaceutically acceptable salt thereof in water, oil or wax phase; poorly soluble polyelectrolyte complexes of glatiramer or a pharmaceutically acceptable salt thereof; "in-situ" gel-forming matrices based on the combination of water-miscible solvent with glatiramer or a pharmaceutically acceptable salt thereof; and biodegradable polymeric microparticles with incorporated glatiramer or a pharmaceutically acceptable salt thereof. Each possibility represents a separate embodiment of the invention. In particular embodiments, the compositions of the present invention are in the form of injectable microparticles wherein the glatiramer or pharmaceutically acceptable salt thereof is entrapped in a biodegradable or non-biodegradable carrier. The microparticulate compositions of the present invention may comprise a water-in oil-in water double emulsion. Within the scope of the present invention is a microparticulate composition comprising an internal aqueous phase comprising glatiramer or any pharmaceutically acceptable salt thereof, an oil phase or water-immiscible phase comprising a biodegradable or non-biodegradable polymer and an external aqueous phase. The external aqueous phase may further comprise a surfactant, preferably polyvinyl alcohol (PVA), polysorbate, polyethylene oxide-polypropylene oxide block copolymers or cellulose esters. The terms "oil phase" and "water-immiscible phase" may be used interchangeably herein.

According to particular embodiments, the long acting pharmaceutical compositions of the present invention are in the form of microparticles prepared by a water-in oil-in water double emulsification process. In currently preferred embodiments, the long acting pharmaceutical compositions of the present invention comprise an internal aqueous phase comprising a therapeutically effective amount of a pharmaceutically acceptable salt of glatiramer, a water immiscible polymeric phase comprising a carrier selected from a biodegradable and a non-biodegradable polymer, and an external aqueous phase. In other currently preferred embodiments, the water immiscible polymeric phase comprises a biodegradable polymer selected from PLA and PLGA. Each possibility represents a separate embodiment of the invention. In additional embodiments, the external aqueous phase comprises a surfactant selected from polyvinyl alcohol (PVA), polysorbate, polyethylene oxide-polypropylene oxide block copolymers and cellulose esters. Each possibility represents a separate embodiment of the invention.

In some embodiments, the compositions may comprise any other pharmaceutically acceptable salt of glatiramer including, but not limited to, sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate and the like salts. Each possibility represents a separate embodiment of the invention.

The copolymers can be made by any procedure available to one of skill in the art. For example, the copolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example, dicyclohexylcarbodiimide, can be used to facilitate the formation of the peptide bond.

Blocking groups can be used to protect functional groups, such as the side chain moieties and some of the amino or carboxyl groups against undesired side reactions. The process disclosed in U.S. Pat. No. 3,849,550, the contents of which are hereby incorporated by reference in its entirety, can be used for preparing the copolymers of the invention. For example, the N-carboxyanhydrides of tyrosine, alanine, γ-benzyl glutamate and N, ε-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by one molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. U.S. Pat. Nos. 6,620,847; 6,362,161; 6,342,476; 6,054,430; 6,048,898 and 5,981,589, the content of which are hereby incorporated by reference in their entirety, disclose improved methods for preparing glatiramer acetate (Cop-1). For purposes of this application, the terms "ambient temperature" and "room temperature" typically means a temperature ranging from about 20° C. to about 26° C.

Long-acting and depot formulations of GA are disclosed for example in U.S. Pat. No. 8,377,885. In a non-limiting example, GA Depot is an aseptic lyophilized powder comprising polyglactin microparticles loaded with GA. This formulation is suspended in water for injection and is intended for intra-muscular administration once every 4 weeks for example.

The molecular weight of the copolymers can be adjusted during polypeptide synthesis or after the polymers have been made. To adjust the molecular weight during polypeptide synthesis, the synthetic conditions or the amounts of amino acids are adjusted so that synthesis stops when the polypeptide reaches the approximate desired length. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the copolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by the test reaction. The trifluoroacetyl-polypeptide with the desired molecular weight profile is then further treated with an aqueous piperidine solution to form a deprotected polypeptide having the desired molecular weight.

In a currently preferred embodiment, a test sample of protected polypeptide from a given batch is reacted with hydrobromic acid for about 10-50 hours at a temperature of about 20-28° C. The best conditions for that batch are determined by naming several test reactions. For example, in one embodiment, the protected polypeptide is reacted with hydrobromic acid for about 17 hours at a temperature of about 26° C.

In certain embodiments, the dosage forms include, but are not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(ε-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-{carboxyphenoxy} propane), CPP; poly(p-{carboxyphenoxy}hexane) s CPH; polyamines, polyurethanes, polyesteramides, polyorthoesters {CHDM: cis/trans-cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) triblock copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. Each possibility represents a separate embodiment.

Currently preferred biodegradable polymer is a lactic acid-based polymer, more preferably polylactide, or poly (D, L-lactide-co-glycolide) i.e. PLGA. Preferably, the biodegradable polymer is present in an amount between about 10% to about 98% w/w of the composition. The lactic acid-based polymer has a monomer ratio of lactic acid to glycolic acid in the range of 100:0 to about 0:100, preferably 100:0 to about 10:90 and has an average molecular weight of from about 1,000 to 200,000 daltons. However, it is understood that the amount of biodegradable polymer is determined by parameters such as the duration of use and the like.

The compositions of the present invention may further comprise one or more pharmaceutically acceptable excipient(s) selected from, but not limited to, co-surfactants, solvents/co-solvents, water immiscible solvents, water, water miscible solvents, oily components, hydrophilic solvents, emulsifiers, preservatives, antioxidants, anti-foaming agents, stabilizers, buffering agents, pH adjusting agents, osmotic agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween®), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention. Suitable solvents/co-solvents include, but not limited to, alcohols, triacetin, dimethyl isosorbide, glycofurol, propylene carbonate, water, dimethyl acetamide, and the like or mixtures thereof. Each possibility represents a separate embodiment of the invention. Suitable anti-foaming agents include, but are not limited to, silicon emulsions or sorbitan sesquioleate. Suitable stabilizers to prevent or reduce the deterioration of the components in the compositions of the present invention include, but are not limited to, antioxidants such as glycine, α-tocopherol or ascorbate, BHA, BHT, and the like or mixtures thereof. Each possibility represents a separate embodiment of the invention. Suitable tonicity modifiers include, but are not limited to, mannitol, sodium chloride, and glucose. Each possibility represents a separate embodiment of the invention. Suitable buffering agents include, but are not limited to, acetates, phosphates, and citrates with suitable cations. Each possibility represents a separate embodiment of the invention.

The compositions of the present invention can be prepared by any manner known in the art. Currently preferred is the incorporation of the glatiramer or salt thereof copolymer into a colloidal delivery system, e.g., biodegradable microparticles, thus allowing release retardation by diffusion through polymeric walls of the particle and by polymer degradation in water media or biological fluids in the body. The compositions of the present invention can be prepared in the form of injectable microparticles by a process known as the "double emulsification". Briefly, the concentrated solution of the water-soluble copolymer is dispersed in a solution of the biodegradable or non-biodegradable polymer in water-immiscible volatile organic solvent (e.g. methylene chloride, chloroform and the like). The thus obtained "water-in-oil" (w/o) emulsion is then dispersed in a continuous external water phase containing surfactant (e.g. polyvinyl alcohol—PVA, polysorbates, polyethylene oxide-polypropylene oxide block copolymers, cellulose esters and the like) to form "water-in oil-in water (w/o/w) double emulsion" droplets. After evaporation of the organic solvent, the microparticles solidify and are collected by filtration or centrifugation. The collected microparticles (MPs) are washed with purified water to eliminate most of the surfactant and non-bonded peptide and centrifugated again. The washed MPs are collected and lyophilized without additives or with the addition of cryoprotectant (mannitol) to facilitate their subsequent reconstitution.

The particle size of the "water-in oil-in water (w/o/w) double emulsion" can be determined by various parameters including, but not limited to, the amount of applied force at this step, the speed of mixing, surfactant type and concentration, etc. Suitable particle sizes range from about 1 to 100 μm.

The depot systems of the present invention encompass any forms known to a person of skill in the art. Suitable forms include, but are not limited to, biodegradable or non biodegradable microspheres, implants of any suitable geometric shape, including implantable rods, implantable capsules, and implantable rings. Each possibility represents a separate embodiment of the invention. Further contemplated are prolonged release gel depot and erodible matrices. Each possibility represents a separate embodiment of the invention. Suitable implantable systems are described for example in US 2008/0063687, the content of which is hereby incorporated in its entirety. Implantable rods can be prepared as is known in the art using suitable micro-extruders.

According to the principles of the present invention, the long acting pharmaceutical compositions of the present invention provide equal or superior therapeutic efficacy to the commercially available daily injectable dosage forms, with reduced incidence of side effects and with reduced severity of side effects at the local and/or systemic level. In some embodiments, the compositions of the present invention provide prolonged release or prolonged action of glatiramer in a subject as compared to a substantially similar dose of an immediate release formulation of glatiramer acetate.

Encompassed by the present invention is a combination therapy of glatiramer acetate or any other pharmaceutically acceptable salt of glatiramer with adipose-derived stem cells and optionally at least one other active agent. Active agents within the scope of the present invention include, but are not limited to interferons, e.g. pegylated or non-pegylated α-interferons, or β-interferons, e.g. interferon β-1a or interferon β-1b, or τ-interferons; immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH; adenosine deaminase inhibitors, e.g. cladribine; IV immunoglobulin G (e.g. as disclosed in Neurology, 1998, May 50(5):1273-81) monoclonal antibodies to various T-cell surface markers, e.g. natalizumab (ANTEGREN®) or alemtuzumab; TH2 promoting cytokines, e.g. IL-4, IL-10, or compounds which inhibit expression of TH1 promoting cytokines, e.g. phosphodiesterase inhibitors, e.g. pentoxifylline; antispasticity agents including baclofen, diazepam, piracetam, dantrolene, lamotrigine, rifluzole, tizanidine, clonidine, beta blockers, cyproheptadine, orphenadrine or cannabinoids; AMPA glutamate receptor antagonists, e.g. 2,3-dihydroxy-6-nitro-7-sulfamoylbenzo(f)quinoxaline, [1,2,3,4,-tetrahydro-7-morpholin-yl-2,3-dioxo-6-(trifluoromethyl)quinoxalin-i-yl] methylphosphonate, 1-(4-aminophenyl)-4-methyl-7,8-methylene-dioxy-5H-2,3-benzodiazepine, or (−)1-(4-aminophenyl)-4-methyl-7,8-methylene-dioxy-4,5-dihydro-3-methylcarbamoyl-2,3-benzodiazepine; inhibitors of VCAM-1 expression or antagonists of its ligand, e.g. antagonists of the α4β1 integrin VLA-4 and/or α-4-β-7 integrins, e.g. natalizumab (ANTEGREN®); anti-macrophage migration inhibitory factor (Anti-MIF); xii) Cathepsin S inhibitors; xiii) mTor inhibitors. Each possibility represents a separate embodiment of the invention. Currently preferred one other active agent is FTY720 (2-amino-2-[2-(4-octylphenyl)ethyl] propane-1,3-diol; fingolimod) belonging to the class of immunosuppressants.

The present invention encompasses the use of glatiramer acetate or any other pharmaceutically acceptable salt of glatiramer in depot form suitable for implantation into an individual in need thereof for treating multiple sclerosis, together with administration of ADSCs.

The present invention encompasses a pharmaceutical composition comprising glatiramer acetate, or any other pharmaceutically acceptable salt of glatiramer, the pharmaceutical composition being in a sustained release depot form, for use with hADSCs in the treatment of multiple sclerosis.

The invention also encompasses the combination of glatiramer acetate and ADSCs, with at least one additional drug, preferably, an immunosuppressant, particularly fingolimod.

The present invention further encompasses the use of glatiramer acetate in sustained-release depot form suitable for administration or implantation to/into a subject in need thereof, for the manufacture of a medicament for use with hADSCs in the treatment of multiple sclerosis.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Effect of GA Depot and Human ADSCs on MOG-Induced Chronic EAE in C57BL/6 Mice Materials and Methods Glatiramer Acetate:
(Commercial name Copaxone®) 20 mg/ml in pre-filled syringes, Teva Pharmaceutical Industries Ltd., Petah-Tikva, Israel). Injected subcutaneously (SC).

Glatiramer Acetate (GA) Depot Production and GA Release Profile:
GA Depot was prepared as described in U.S. Pat. No. 8,377,885, lyophilized and stored. The release profile of GA from the GA Depot formulation was determined as follows: a known amount of the lyophilized GA Depot powder was suspended in phosphate buffered saline (PBS) and stirred at 37° C. for 34 days. At regular intervals, a sample was recovered from the stirred suspension and the amount of GA was determined using gel permeation chromatography (GPC). Percentage content of GA was calculated based on the known amount of GA Depot in the suspension. For administration (intramuscularly, IM), the lyophilized GA Depot powder was suspended in sterile water for injection (WFI).

Human Adipose Derived Stem Cells (ADSCs) Isolation, Characterization, Culture and Preparation for Intracerebroventricular (ICV) Injection:

Protocol of Cell Preparation:

ADSCs Isolation:

Lipoaspirate derived from human tissue was washed 4 times with an equal volume of PBS at room temperature (RT). The lipoaspirate was then digested with collagenase (NB4, Serva) at 37° C. for 30 minutes with shaking. Subsequently, the digested sample was centrifuged at RT, 300-500 g, for 10 min, and the upper fluid was removed including undigested fat. The reaction was stopped by adding an equal volume of a xeno-free expansion medium (StemMACS™, Miltentyi) followed by an additional centrifugation at RT, 500 g for 10 minutes. The resulting pellet was transferred to a 50 ml centrifuge tube, washed with medium and centrifuged at the same conditions. The supernatant was removed and the pellet resuspended with 25 ml of red blood cell lysis buffer (Sigma-Aldrich, St. Louis, Mo., USA) for 10 minutes at RT. Twenty five (25) ml of PBS were added and the sample centrifuged at 500 g for 5 minutes. The pellet was resuspended with 10 ml medium and filtered through a 100 µm filter, followed by the addition of additional 10 ml medium. The solution was centrifuged at 500 g for 5 minutes. The procedure was repeated with a 40 µm filter and the cells were counted. The resulting cells are referred as stromal vascular fraction (SVF).

Cell Culture:

SVF was plated at a density of ~2×10$^6$ cells per 75 cm$^2$. Cells were grown to ~80% confluency, trypsinized and sub-cultured up to passage 3-4. Cells were then collected and analyzed by FACS for the markers: CD105, CD73, CD90, CD45, CD44, CD19, CD11B, HLADR and CD34. The cells were stored frozen in liquid nitrogen until use. For use, frozen cells were thawed and plated at a concentration of 50,000 cells/cm$^2$ and incubated overnight. Prior to cells ICV injection the cells were trypsinized, counted and prepared for injection at a concentration of 2×10$^5$ cell/4 µl PBS and kept in ice until use for a period no longer than 30 min. ICV injection was performed using a stereotactic system and care was taken not to injure the mice brain.

Animals:

All animal studies were approved by local ethics committees. C57BL/6 female mice, 7-9 weeks old were randomized into control or treatment groups with similar mean weight. Animals were given food and water ad libitum throughout the experiment.

Induction of Experimental Autoimmune Encephalomyelitis (EAE):

In order to induce EAE, an emulsion of myelin-oligodendrocyte-glycoprotein (MOG) 35-55 (GL Biochem co. Ltd, Shanghai, China) in modified Complete Freund's Adjuvant (CFA) (Sigma-Aldrich, St. Louis, Mo., USA) was prepared as follows: heat-killed *M. tuberculosis* strain H37RA (Sigma) was added to CFA reaching a final concentration of 4 mg/mL. Subsequently, 2 mg/mL MOG 35-55 were emulsified with an equal amount of modified CFA. EAE had been induced by injection of this emulsion subcutaneously (SC) on the shaved back of the mouse at one site, followed by an intraperitoneal injection of *Bordetella pertussis* toxin (Sigma) in PBS on Day 0, and 48 hours post MOG immunization.

Measurements:

Body weight was measured daily from onset of disease symptoms to Day 28. EAE was assessed by clinical scoring of the mice once daily from Day 0 to Day 28 post-immunization (Table 1). Dead animals received a clinical score of 5 and the last weight measurement before animal death was recorded as final weight.

TABLE 1

EAE Clinical Score

| Score | Clinical Signs |
|---|---|
| 0 | Normal mouse; no overt signs of disease |
| 1 | Limp tail |
| 2 | Hind limb paralysis |
| 3 | Hind and front limb paralysis |
| 4 | Complete paralysis: sacrifice for humane reasons |
| 5 | Moribund state; Death by EAE |

The following calculations were derived from clinical score raw data:

Mean Maximum Score:

is the mean of the highest scores noted for each mouse in a specific group up to an indicated day of analysis.

Mean Disease Duration:

sum of (day of analysis–day of disease onset for each mouse)/(number of mice per group)

Mean Day of Onset:

sum of day of disease onset of each mouse/number of mice per group

Area Under the Curve (AUC) of Clinical Score:

calculated using Microsoft Excel and represents disease burden.

Experimental Design:

The experimental design of the EAE model is detailed in Table 2 (n=10 in each group).

TABLE 2

Experimental design

| Group | Test article | Administration route | Dose | Days of administration | Solvent |
|---|---|---|---|---|---|
| 1 | Control, WFI | SC | N/A | 0-8 | WFI, 0.2 ml |
| 2 | GA Depot 10 mg* | IM | 10 mg | 0.1** | WFI, 0.2 ml |
| 3 | GA Depot 2 mg | IM | 2 mg | 0 | WFI, 0.2 ml |
| 4 | ADSCs | ICV | 2 × 10^5 | 0 | PBS, 4 µl |
| 5 | GA Depot 10 mg and ADSCs | IM ICV | 10 mg 2 × 10^5 | 0.1* 0 | WFI, 0.2 ml PBS, 4 µl |

TABLE 2-continued

| | | Experimental design | | | |
|---|---|---|---|---|---|
| Group | Test article | Administration route | Dose | Days of administration | Solvent |
| 6 | GA Depot 2 mg and ADSCs | IM ICV | 2 mg 2 × 10^5 | 0 0 | WFI, 0.2 ml PBS, 4 μl |
| 7 | Copaxone^R | SC | 2 mg | 0-8 | WFI, 0.1 ml |

*Doses of GA Depot are given according to the amount of the active ingredient, i.e., GA Depot 10 mg contains 10 mg GA);
**Due to technical considerations, this dose was divided into two 5 mg doses that were administered on days 0 and 1.

Statistical Analysis:

Each data set was analyzed using single-factor analysis of variance (ANOVA) followed by two-tailed 'two-sample students' T test assuming unequal variances, n=10/group, +/−standard error.

Results

The results of the trial, calculated up to 28 days from the first injection of the test articles, are described in Table 3 and FIGS. 1-5.

Phenotype of the Cells:

| Marker (dye) | % expression |
|---|---|
| CD73 (PE*) | 100 |
| CD90 (PE) | 100 |

-continued

| Marker (dye) | % expression |
|---|---|
| CD105 (PE) | 100 |
| CD44 (FITC**) | 100 |
| HLADR (PE) | 0.1 |
| CD34 (PE) | 1.5 |
| CD45 (PE) | 0.5 |
| CD11b (PE) | 0.2 |
| CD19 (PE) | 0.1 |
| IgG1 (PE) | 0.2 |
| IgG2a (PE) | 0.1 |
| IgG1 (FITC) | 0 |

TABLE 3

Effect of GA Depot and ADSCs on EAE

| Group | Mean maximum Score | Mean disease duration | Mean day of onset | AUC clinical score | Survival rate (Day 28) |
|---|---|---|---|---|---|
| 1. Control (WFI, SC) | 3.45 ± 0.30 | 18.60 ± 0.31 | 9.40 ± 0.31 | 44.58 ± 4.48 | 80% |
| 2. GA Depot 10 mg IM | 3.60 ± 0.32 | 15.40 ± 0.64 | 12.60 ± 0.64 | 36.55 ± 3.20 | 70% |
| 3. GA Depot 2 mg IM | 3.50 ± 0.27 | 16.30 ± 0.60 | 11.70 ± 0.60 | 38.45 ± 2.64 | 80% |
| 4. ADSCs 2 × 10^5 ICV | 2.75 ± 0.19 | 17.30 ± 0.45 | 10.70 ± 0.45 | 35.00 ± 2.68 | 100% |
| 5. GA Depot 10 mg and ADSCs 2 × 10^5 | 2.55 ± 0.40 | 12.80 ± 1.45 | 14.60 ± 1.01 | 27.88 ± 5.48 | 90% |
| 6. GA Depot 2 mg and 2 × 10^5 ADSCs | 2.45 ± 0.25 | 14.50 ± 1.61 | 13.50 ± 1.61 | 27.40 ± 3.23 | 100% |
| 7. Copaxone ® 2 mg · day, SC | 4.10 ± 0.31 | 16.70 ± 0.61 | 11.30 ± 0.65 | 46.20 ± 6.95 | 50% |

Statistical Analysis is Detailed Below.

TABLE 4

Figure 4:
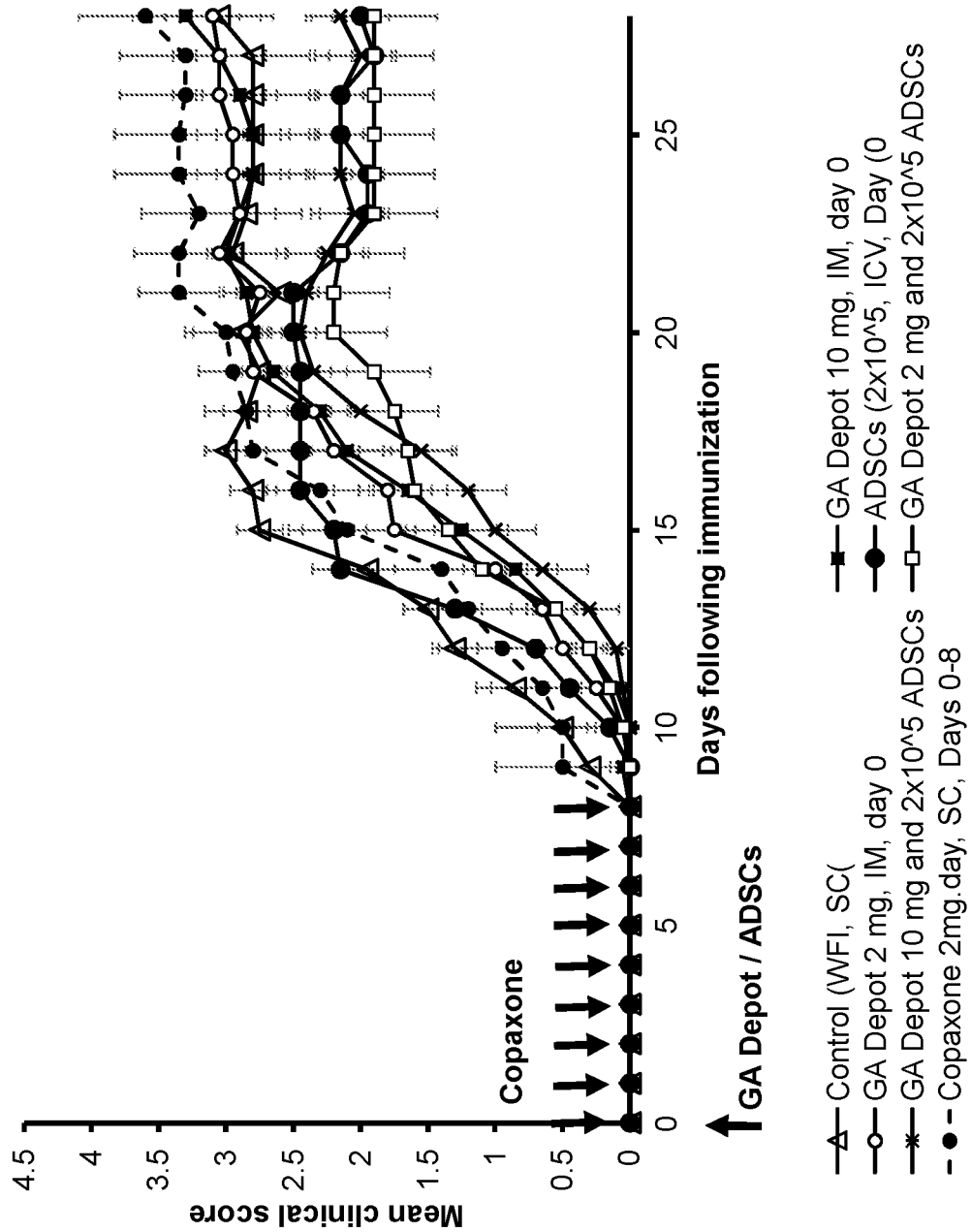
FIG. 4: Effect of GA Depot and ADSCs on EAE as determined by Mean Clinical Score analysis up to day 28. Mean clinical score 0-28 days following immunization with: control (water for injection SC), GA Depot, 2 mg IM; GA Depot, 10 mg IM; ADSCs $2\times10^5$ cells ICV; GA Depot 10 mg IM and ADSCs $2\times10^5$ cells ICV; GA Depot 2 mg IM and ADSCs $2\times10^5$ cells ICV; Copaxone® (immediate release glatiramer acetate) 2 mg SC. n=10/group, +/−standard error. See table 4 for statistical analysis.
Figure 5:
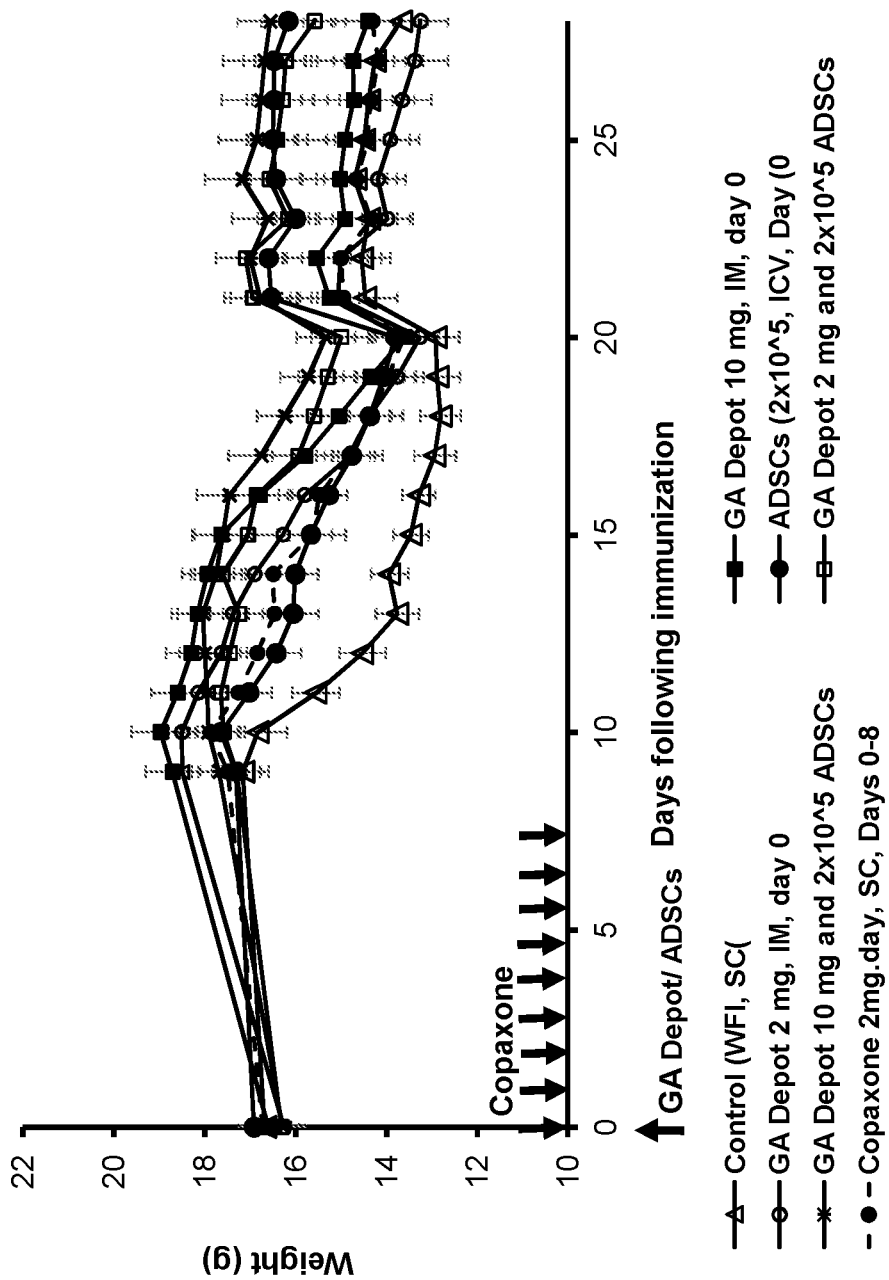
FIG. 5: Effect of GA Depot and ADSCs on weight of MOG-induced EAE mice up to day 28. Body weight was measured daily from day 0 to day 28. For dead animals the last weight measurement before animal death was recorded as final weight. n=10/group, +/−standard error. Refer to table 5 for statistical analysis.
Figure 6:
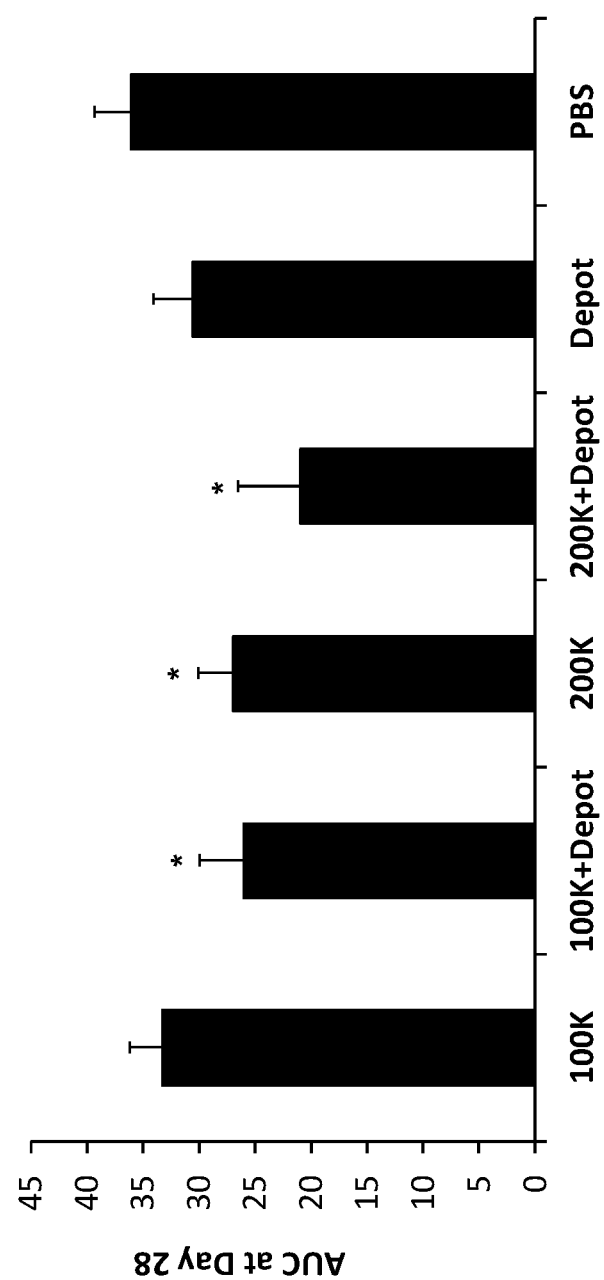
FIG. 6: Effect of GA Depot in combination with the indicated doses of ADSCs on EAE as determined by AUC Clinical Score analysis up to day 28. *P<0.05 compared with PBS.
Figure 7:
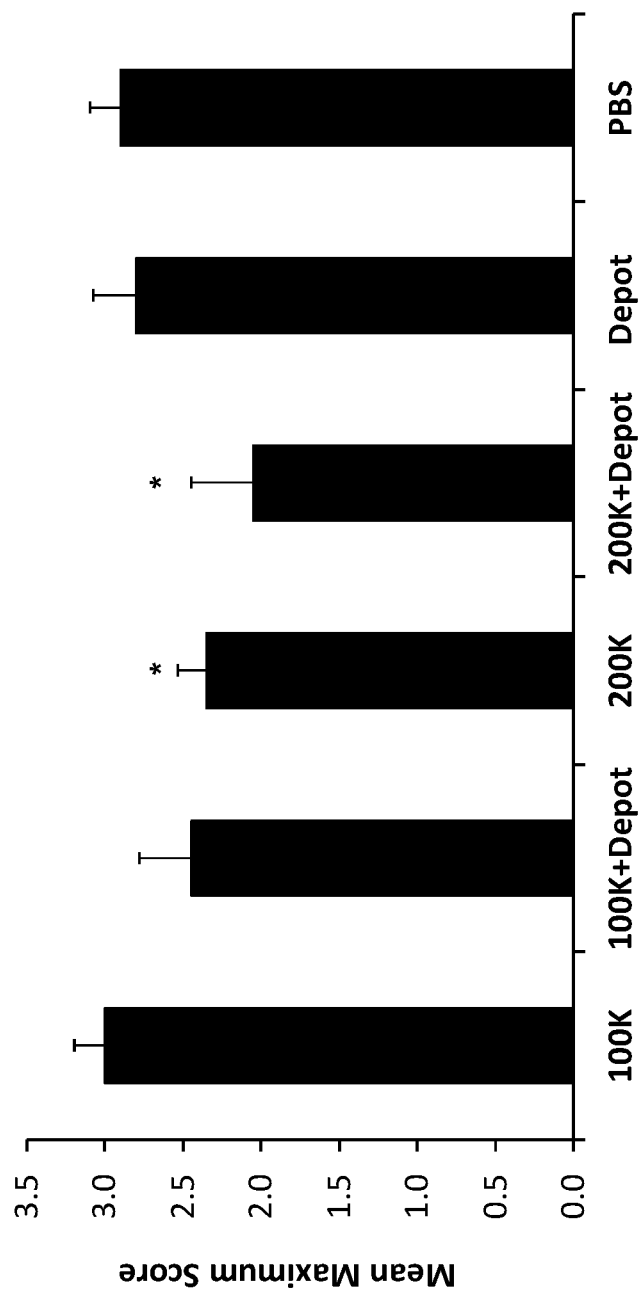
FIG. 7: Effect of GA Depot in combination with the indicated doses of ADSCs on EAE as determined by Mean Maximum Score analysis up to day 28. *P<0.05 compared with PBS.
Figure 8:
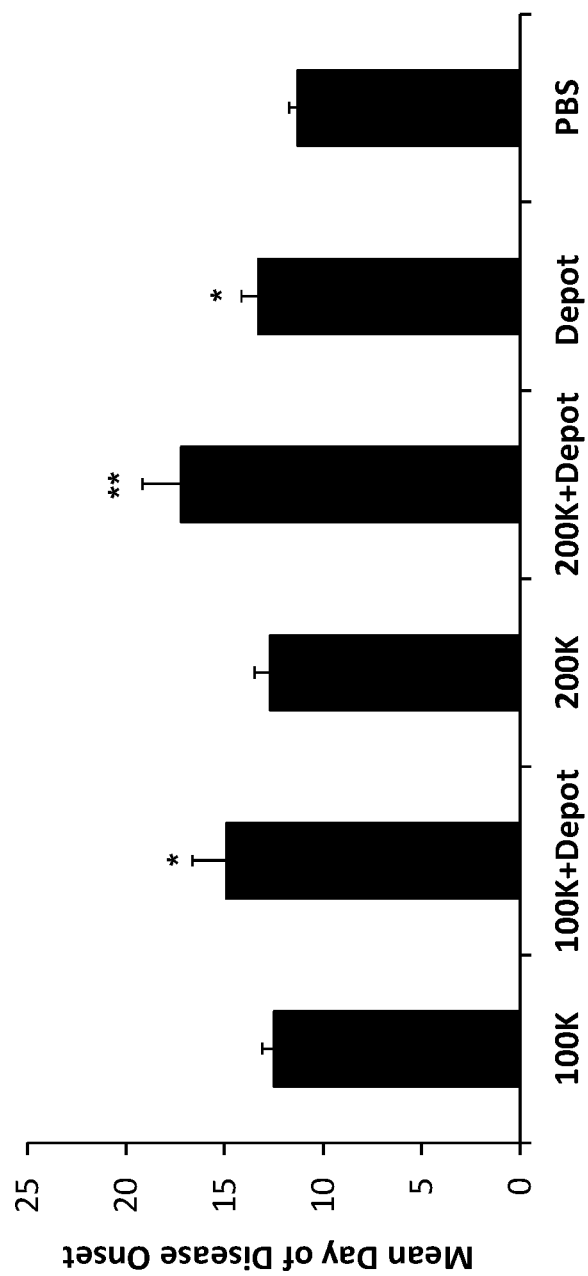
FIG. 8: Effect of GA Depot in combination with the indicated doses of ADSCs on EAE as determined by Mean Day of Disease Onset analysis up to day 28. ** P<0.05 compared with 200K, Depot, PBS; *P<0.05 compared with PBS.
Figure 9:
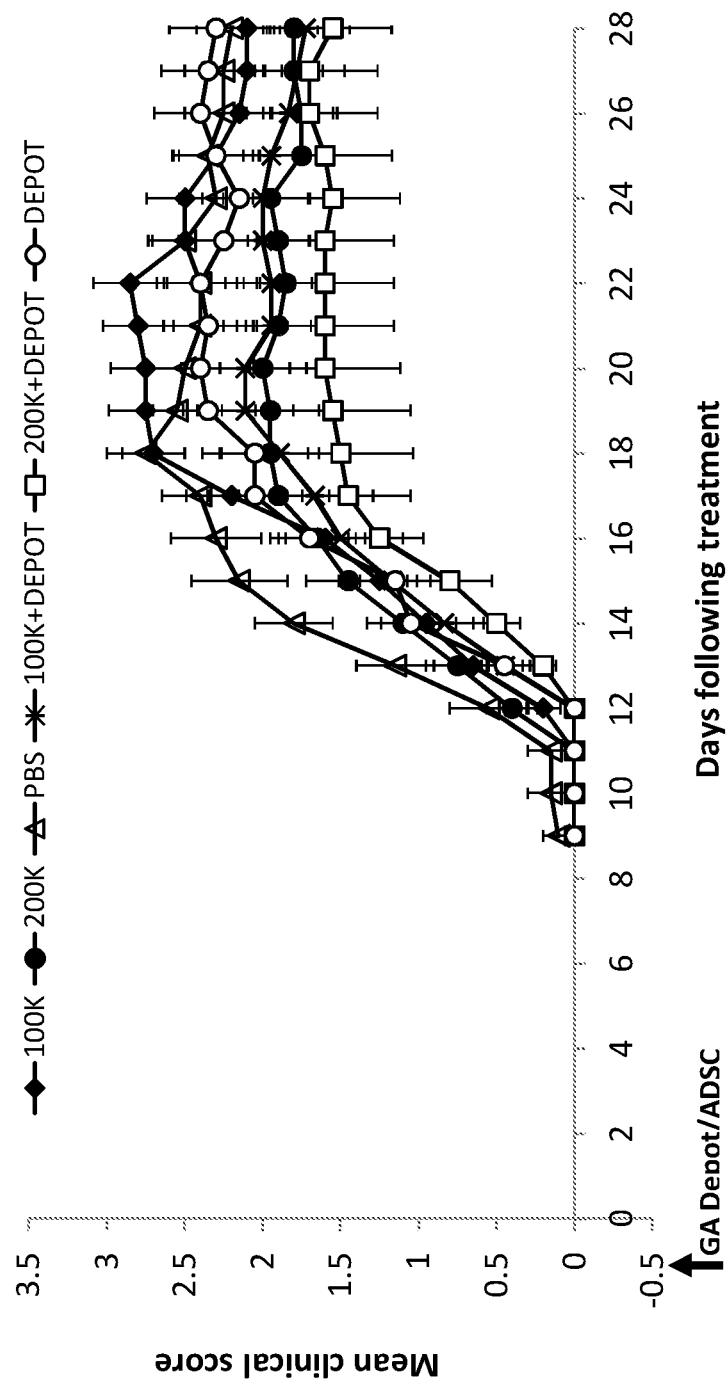
FIG. 9: Effect of GA Depot in combination with the indicated doses of ADSCs on EAE as determined by Mean Clinical Score analysis up to day 28. +/−standard error.
Figure 10:
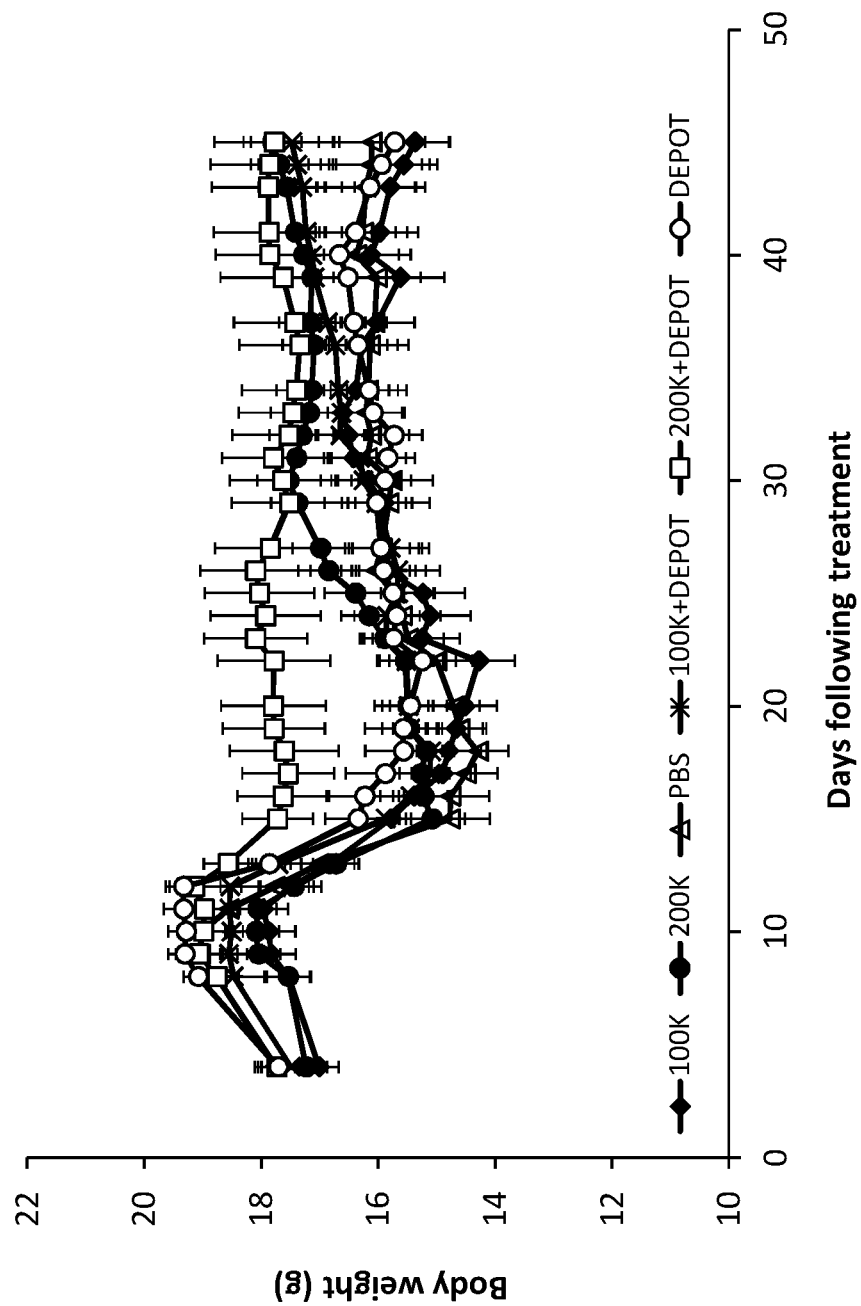
FIG. 10: Effect of GA Depot in combination with the indicated doses of ADSCs on body weight of MOG-induced EAE mice. Body weight was followed-up to day 45. Body weight was measured daily from day 0 to day 45. For dead animals the last weight measurement before animal death was recorded as final weight. n=10/group, +/−standard error.

Statistical analysis of Mean Clinical Score (FIG. 4)

| ay | *P < 0.05, single factor ANOVA followed by one-tail two-sample T test assuming unequal variances, n = 10/group, +/−standard error |
|---|---|
| | WFI compared with GA Depot 2 mg and 10 mg, with or without ADSCs; all compared to GA Depot 2 or 10 mg with cells except Copaxone |
| 2 | WFI compared with all except Copaxone; GA Depot 10 mg and ADSCs compared with ADSCs |
| 3 | WFI compared with all except ADSCs and Copaxone; ADSCs compared with GA Depot 10 mg, GA Depot 10 mg and ADSCs and GA Depot 2 mg and ADSCs |
| 4 | WFI compared with all except ADSCs and Copaxone; ADSCs with all except from WFI and Copaxone |
| 5 | WFI compared with all except ADSCs and Copaxone; ADSCs compared with GA Depot 10 mg, GA Depot 10 mg and ADSCs and GA Depot 2 mg and ADSCs |
| 6, 17 | WFI compared with all except Copaxone; ADSCs compared with GA, GA Depot 10 mg and ADSCs and GA Depot 2 mg and ADSCs |
| 8 | WFI compared with all except ADSCs and Copaxone; GA Depot 2 mg and ADSCs compared with all, GA Depot 10 mg and ADSCs compared with Copaxone |
| 2 | ADSCs compared with all except GA Depot 2 or 10 mg with ADSCs; GA Depot 2 mg with ADSCs compared to GA Depot 2 or 10 mg and Copaxone |

TABLE 4-continued

Statistical analysis of Mean Clinical Score (FIG. 4)

*P < 0.05, single factor ANOVA followed by one-tail two-sample T test
ay  assuming unequal variances, n = 10/group, +/−standard error

| | |
|---|---|
| 3, 24 | ADSCs compared with all except GA Depot 2 or 10 mg with ADSCs; GA Depot 2 mg with ADSCs compared to all except GA Depot 10 mg and ADSCS and compared to ADSCs |
| 6 | ADSCs compared with GA Depot 2 or 10 mg and with Copaxone; GA Depot 2 mg with ADSCs compared to all except GA Depot 10 mg and ADSCS and compared to ADSCs |
| 7, 28 | ADSCs compared with all except GA Depot 2 or 10 mg with ADSCs; GA Depot 2 mg with ADSCs compared to all except GA Depot 10 mg and ADSCS and compared to ADSCs |

15

TABLE 5

Statistical analysis of Mean Clinical Score (FIG. 5)
*P < 0.05, single factor ANOVA followed by one-tail two-sample
T test assuming unequal variances, n = 10/group, +/−standard error WFI compared with all groups; GA Depot 10 mg compared with ADSCs
and Copaxone; GA Depot 2 mg compared with Copaxone
WFI compared with all groups; GA Depot 10 mg compared with ADSCs
WFI compared with all groups; GA Depot 10 mg and ADSCs compared
with ADSCs and with GA Depot 2 mg
WFI compared with ADSCs and GA Depot 2 mg or 10 mg and ADSCs; GA
Depot 2 mg compared to GA Depot 2 or 10 mg and ADSCs; ADSCs compared with
GA Depot 10 mg and ADSCs
WFI compared with ADSCs and GA Depot 2 mg or 10 mg and ADSCs; GA
Depot 2 mg compared to GA Depot 2 or 10 mg and ADSCs; GA Depot 10 mg
compared to ADSCs and GA Depot 2 mg and ADSCs
WFI compared with ADSCs and GA Depot 2 mg or 10 mg and ADSCs; GA
Depot 2 mg compared to GA Depot 2 or 10 mg and ADSCs; GA Depot 10 mg
compared to GA Depot 2 mg and ADSCs
ADSCs compared with GA Depot 2 mg or 10 mg and with WFI; GA Depot
10 mg with ADSCs compared to GA Depot 2 or 10 mg and with WFI; GA Depot 2 mg
with ADSCs compared to GA Depot 10 mg and with WFI ADSCs alone showed beneficial effects on the maximum disease score and disease burden, as reflected by the lower Mean Maximum Score and AUC of clinical score compared to control (WFI). The beneficial effect on disease score started only around Day 20. ADSCs alone did not show an effect on disease onset compared to control.

GA Depot 2 mg/10 mg alone showed a beneficial effect on disease onset compared to control. The Depot alone did not show an effect on the maximum disease score or disease burden.

The combination of ADSCs and GA Depot 2 mg/10 mg showed beneficial effects on the maximum disease score and disease burden compared to control, as well as delayed the onset of the disease. Importantly, the combinations showed a slower increase in the clinical score throughout the experiment (i.e., slower disease progression), at some points compared to all other groups, indicating synergism between the components. Unexpectedly, the combination of ADSCs and the lower dose GA depot (2 mg depot) was particularly beneficial in this respect.

The experimental data show a clear advantage of GA Depot injected IM alongside ADSCs injected ICV. The combined use of GA Depot and ADSCs yielded a long term effect on the attenuation of EAE symptoms that led to a significant reduction of disease burden.

Example 2—Dose Response of ADSCs

In order to assess the cell dose therapeutic effect of ADSCs in MOG-induced EAE (as described above), different amounts ($1 \times 10^5$ or $2 \times 10^5$) of ADSCs were used for ICV administration, alone or in combination with IM injection of 2 mg GA depot. The experimental design is detailed in Table 6 (n=10 in each group).

TABLE 6

Experimental design

| Group | Test article | Adm. route | Dose | Days of administration | Vehicle, injection volume |
|---|---|---|---|---|---|
| 1 | ADSCs | ICV | $1 \times 10^5$ | 0 | PBS 4 ul |
| 2 | ADSCs | ICV | $2 \times 10^5$ | 0 | PBS 4 ul |
| 3 | Control (PBS) | ICV | N/A | 0 | PBS 4 ul |
| 4 | ADSCs + GA Depot | ICV + IM | $1 \times 10^5$ + 2 mg | 0 0 + 1 | PBS 4 ul + 0.1 ml |
| 5 | ADSCs + GA Depot | ICV + IM | $2 \times 10^5$ + 2 mg | 0, 0 + 1* | PBS 4 ul + 0.1 ml |
| 6 | GA Depot | IM | 2 mg | 0 + 1 | WFI, 0.1 ml |

*GA depot was divided into two doses that were administered on days 0 and 1.

Results

The results of the trial, calculated up to 28 days from the first injection of the tested articles, are described in FIGS. 6-10.

A cell dose effect was observed, where the higher dose of $2 \times 10^5$ cells was more effective than the $1 \times 10^5$ dose in reducing disease burden and disease score.

Importantly, the combination of ADSCs and GA Depot showed a clear synergistic effect, with a significant delay in disease onset and slower disease progression compared to all other groups.

Example 3—Analyses of Cell Surface Markers of ADSCs

Figure 11:
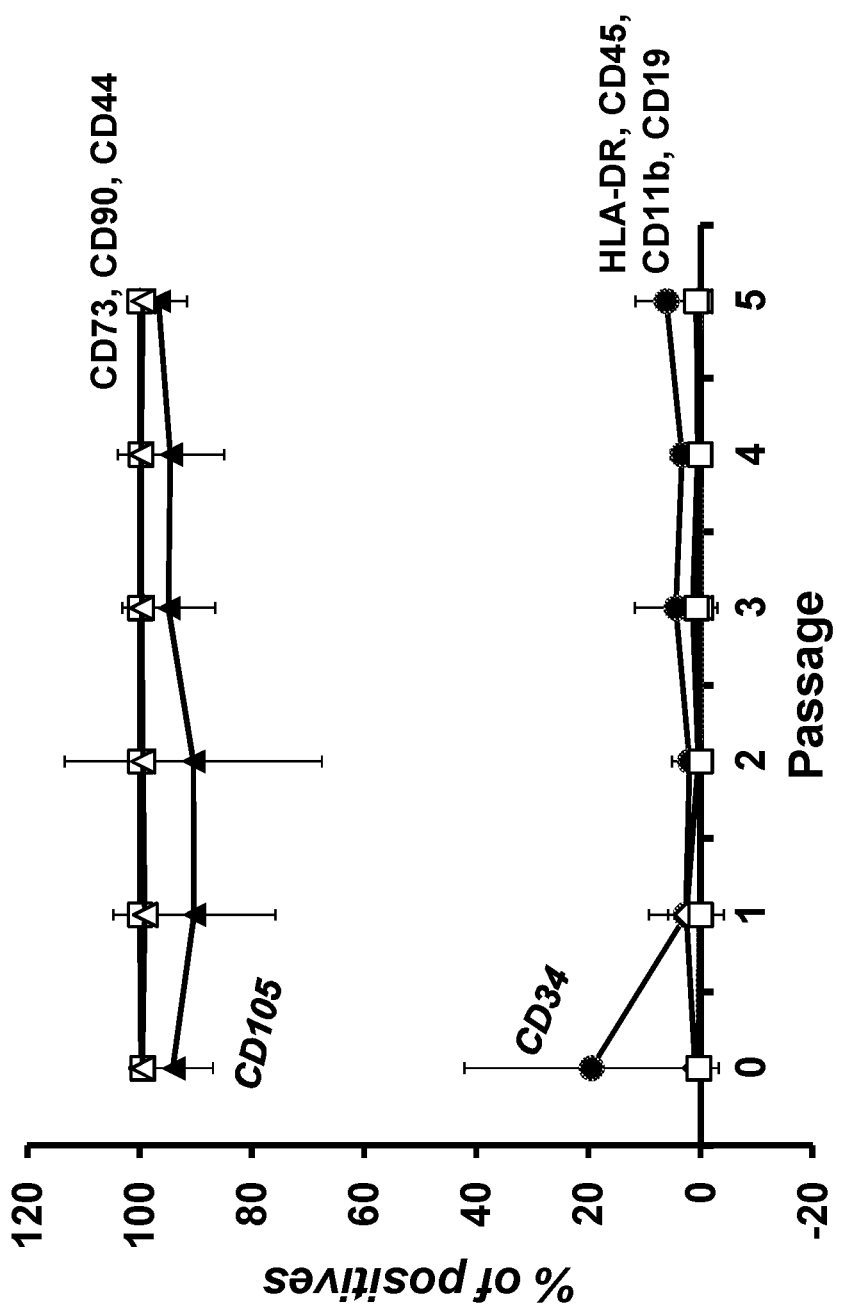
FIG. 11: Cell surface marker expression of ADSCs as a function of passage number. The cells were isolated from adipose tissue and cultured as described in the Examples section, and analyzed for the expression of the indicated markers. The results are the average+/−standard deviation of nine (9) samples.

Tables 7-15 summarize FACS analyses of nine (9) samples of ADSCs prepared as described in Example 1 above, following 1-5 passages. Tables 16-17 and FIG. 11 show the average and standard deviation ("StDev") values. As can be seen in the tables and figure, the markers are stabilized after P3. Passage numbers P3-P4 are equivalent to no more than approximately 14 population doublings.

TABLE 7

Sample 1

| Marker (dye) | 0 | 1 | 2 | 3 | 4 | 5 | |
|---|---|---|---|---|---|---|---|
| CD73 (PE*) | 99.1 | 99.9 | 99.9 | 99.9 | 99.9 | 99.9 | Posi- |
| CD90 (PE) | 97 | 99.9 | 99.9 | 99.9 | 99.9 | 100 | tives |
| CD105 (PE) | 90.4 | 78.3 | 97.8 | 89 | 82.1 | 99.7 | |
| CD44 (FITC**) | 99.6 | 99.8 | 99.9 | 99.9 | 99.7 | 99.8 | |
| HLADR (PE) | 1.2 | 0.2 | 0.1 | 0.1 | 0.4 | 0.1 | Nega- |
| CD34 (PE) | 14.6 | 0.3 | 0.2 | 0.2 | 1.2 | 10.8 | tives |
| CD45 (PE) | 1.5 | 0.1 | 0.1 | 0 | 0.1 | 0.4 | |
| CD11b (PE) | 1.6 | 0.1 | 0 | 0 | 0 | 0 | |
| CD19 (PE) | 0.3 | 0.1 | 0 | 0 | 0 | 0.2 | |
| IgG1 (PE) | 0.3 | 0 | 0.1 | 0 | 0.1 | 0 | Con- |
| IgG2a (PE) | 0.3 | 0.1 | 0.1 | 0 | 0 | 0 | trols |
| IgG1 (FITC) | 0.3 | 0 | 0 | 0 | 0 | 0.1 | |

*PE—Phycoerythrin
**FITC—Fluorescein isothiocyanate

TABLE 8

Sample 2

| Marker (dye) | 0 | 1 | 2 | 3 | 4 | 5 | |
|---|---|---|---|---|---|---|---|
| CD73 (PE) | 99.9 | 100 | 100 | 100 | 100 | 100 | Posi- |
| CD90 (PE) | No data | 100 | 99.9 | 100 | 99.9 | 100 | tives |
| CD105 (PE) | 79.5 | 76.3 | 98.8 | 98.1 | 99.6 | 97.3 | |
| CD44 (FITC) | 99.2 | 99.2 | 99.9 | 99.4 | 99.7 | 99.4 | |
| HLADR (PE) | 0.3 | 0.1 | 0.1 | 0 | 0.1 | 0.2 | Nega- |
| CD34 (PE) | 0.4 | 0.3 | 0.4 | 1.4 | 3.1 | 5 | tives |
| CD45 (PE) | 0.2 | 0 | 0.1 | 0.1 | 0.1 | 0.4 | |
| CD11b (PE) | 0.1 | 0 | 0 | 0 | 0 | 0.1 | |
| CD19 (PE) | 0.1 | 0 | 0 | 0 | 0.1 | 0.4 | |
| IgG1 (PE) | 0.1 | 0.1 | 0 | 0 | 0 | 0.1 | Con- |
| IgG2a (PE) | 0.1 | 0.1 | 0 | 0.1 | 0 | 0 | trols |
| IgG1 (FITC) | 1 | 0 | 0 | 0 | 0 | 0 | |

TABLE 9

Sample 3

| Marker (dye) | 0 | 1 | 2 | 3 | 4 | 5 | |
|---|---|---|---|---|---|---|---|
| CD73 (PE) | 99.8 | 100 | 100 | 100 | 100 | 100 | Posi- |
| CD90 (PE) | 99.9 | 100 | 99.9 | 99.9 | 100 | 100 | tives |
| CD105-PE | 90.8 | 99.9 | 98.3 | 99.4 | 99.3 | 86.9 | |
| CD44 (FITC) | 99.4 | 99.9 | 99.8 | 99.5 | 99.6 | 95.9 | |
| HLADR (PE) | 0.7 | 0.1 | 0 | 0 | 0.1 | 0.1 | Nega- |
| CD34 (PE) | 21.4 | 5 | 1.4 | 6.8 | 7 | 2.3 | tives |

TABLE 9-continued

Sample 3

| Marker (dye) | 0 | 1 | 2 | 3 | 4 | 5 | |
|---|---|---|---|---|---|---|---|
| CD45 (PE) | 0.5 | 20.4 | 0.1 | 0.1 | 2.2 | 1.2 | |
| CD11b (PE) | 0.2 | 0.2 | 0 | 0 | 0.2 | 0 | |
| CD19 (PE) | 0.2 | 0.3 | 0 | 0 | 0.1 | 0.1 | |
| IgG1 (PE) | 0.2 | 0.1 | 0 | 0 | 0.1 | 0 | Con- |
| IgG2a (PE) | 0.2 | 0.1 | 0 | 0 | 0.1 | 0 | trols |
| IgG1 (FITC) | 0.1 | 0 | 0 | 0.1 | 0 | 0 | |

TABLE 10

Sample 4

| Marker (dye) | 0 | 1 | 2 | 3 | 4 | 5 | |
|---|---|---|---|---|---|---|---|
| CD73 (PE) | 99.9 | 99.9 | 99.9 | 100 | 99.9 | 99.9 | Posi- |
| CD90 (PE) | 99.9 | 99.9 | 99.9 | 99.9 | 99.9 | 99.9 | tives |
| CD105-PE | 99.4 | 96.9 | 99.1 | 99.6 | 99.9 | 99.9 | |
| CD44 (FITC) | 99.3 | 98 | 99.5 | 99.5 | 99.4 | 99.8 | |
| HLADR (PE) | 0.2 | 0 | 0.2 | 0 | 0.1 | 0.4 | Nega- |
| CD34 (PE) | 13.6 | 4.8 | 3.3 | 23.1 | 4 | 1.9 | tives |
| CD45 (PE) | 0.7 | 0.1 | 0.2 | 9.7 | 0.3 | 0.2 | |
| CD11b (PE) | 0.2 | 0 | 0 | 0.1 | 0.4 | 0.2 | |
| CD19 (PE) | 0.8 | 0 | 0.1 | 5.7 | 0.5 | 3.5 | |
| IgG1 (PE) | 0.1 | 0 | 0 | 0.1 | 0.1 | 0 | Con- |
| IgG2a (PE) | 0.2 | 0 | 0.1 | 0 | 0 | 0 | trols |
| IgG1 (FITC) | 0.1 | 0 | 0.1 | 0 | 0 | 0 | |

TABLE 11

Sample 5

| Marker (dye) | 0 | 1 | 2 | 3 | 4 | 5 | |
|---|---|---|---|---|---|---|---|
| CD73 (PE) | 99.9 | 100 | 99.8 | 99.9 | 99.9 | 100 | Posi- |
| CD90 (PE) | 99.9 | 100 | 100 | 99.9 | 99.9 | 100 | tives |
| CD105 (PE) | 98.7 | 99.9 | 91.3 | 99.9 | 99.9 | 99.7 | |
| CD44 (FITC) | 98.8 | 99.9 | 97.4 | 99.8 | 100 | 99.9 | |
| HLADR (PE) | 0.4 | 0.1 | 0.2 | 0.1 | 0.1 | 0.1 | Nega- |
| CD34 (PE) | 16.7 | 0.2 | 1.1 | 1.4 | 3.7 | 17.6 | tives |
| CD45 (PE) | 3.4 | 0 | 0.2 | 1.6 | 0.8 | 0.3 | |
| CD11b (PE) | 0.4 | 0.1 | 0.6 | 0 | 0 | 0.1 | |
| CD19 (PE) | 0.3 | 0.1 | 0.1 | 0.2 | 0 | 0.5 | |
| IgG1 (PE) | 0.3 | 0 | 0 | 0 | 0 | 0 | Con- |
| IgG2a (PE) | 0.4 | 0 | 0.1 | 0 | 0 | 0.1 | trols |
| IgG1 (FITC) | 0.2 | 0 | 0 | 0 | 0 | 0 | |

TABLE 12

Sample 6

| Marker (dye) | 0 | 1 | 2 | 3 | 4 | 5 | |
|---|---|---|---|---|---|---|---|
| CD73 (PE) | No data | 99.3 | 99.9 | 99.9 | 99.9 | 100 | Posi- |
| CD90 (PE) | No data | 100 | 100 | 100 | 99.9 | 100 | tives |
| CD105(PE) | No data | 61.7 | 29.7 | 75.1 | 74.4 | 96.2 | |
| CD44 (FITC) | No data | 94.5 | 98.4 | 98.9 | 99.7 | 99.8 | |
| HLADR (PE) | No data | 0.1 | 0.1 | 0 | 0.1 | 0.1 | Nega- |
| CD34 (PE) | No data | 9.5 | 1 | 2.4 | 5.5 | 9.7 | tives |
| CD45 (PE) | No data | 1.7 | 0.5 | 0.9 | 0.8 | 2.4 | |
| CD11b (PE) | No data | 0 | 0.1 | 0 | 0 | 0.7 | |
| CD19 (PE) | No data | 0.1 | 0 | 0.4 | 0.3 | 2.3 | |
| IgG1 (PE) | No data | 0.1 | 0 | 0.1 | 0.1 | 0.3 | Con- |

TABLE 12-continued

Sample 6

| Marker (dye) | Passage | | | | | |
|---|---|---|---|---|---|---|
| | 0 | 1 | 2 | 3 | 4 | 5 |
| IgG2a (PE) | No data | 0.2 | 0.2 | 0.1 | 0.1 | 0.2 trols |
| IgG1 (FITC) | No data | 0 | 0 | 0 | 0 | 0 |

TABLE 13

Sample 7

| Marker(dye) | Passage | | | | | |
|---|---|---|---|---|---|---|
| | 0 | 1 | 2 | 3 | 4 | 5 |
| CD73 (PE) | 99.9 | 100 | 100 | 99.9 | 100 | 99.9 Posi- |
| CD90 (PE) | 99.9 | 100 | 100 | 99.9 | 99.1 | 100 tives |
| CD105 (PE) | 99.7 | 99.9 | 99.5 | 99.9 | 99.1 | 100 |
| CD44 (FITC) | 99.9 | 100 | 99.8 | 99.7 | 99.8 | 99.9 |
| HLADR (PE) | 0.3 | 0.2 | 0.2 | 0.2 | 0.1 | 0.1 Nega- |
| CD34 (PE) | 12 | 0.9 | 10.1 | 0.4 | 3.6 | 0.7 tives |
| CD45 (PE) | 0.9 | 0.5 | 2.1 | 0.2 | 0.2 | 0.3 |
| CD11b (PE) | 0.1 | 0.1 | 0.6 | 0.1 | 0.1 | 0.1 |
| CD19 (PE) | 0.7 | 0.2 | 0.2 | 0.2 | 0.4 | 0.1 |
| IgG1 (PE) | 0.2 | 0.1 | 0.2 | 0.2 | 0.2 | 0.1 Con- |
| IgG2a (PE) | 0.3 | 0.2 | 0.1 | 0.1 | 0.1 | 0.1 trols |
| IgG1 (FITC) | 0.2 | 0 | 0.1 | 0 | 0.1 | 0.1 |

TABLE 14

Sample 8

| Marker (dye) | Passage | | | | | |
|---|---|---|---|---|---|---|
| | 0 | 1 | 2 | 3 | 4 | 5 |
| CD73 (PE) | 99.7 | 100 | 99.7 | 99.8 | 99.7 | 99.9 Posi- |
| CD90 (PE) | 99.5 | 99.8 | 99.8 | 99.8 | 99.7 | 99.9 tives |
| CD105 (PE) | 94 | 99.9 | 99.7 | 92.9 | 95.9 | 89.7 |
| CD44 (FITC) | 99.9 | 100 | 100 | 100 | 100 | 99.9 |
| HLADR (PE) | 0.5 | 0.1 | 0.1 | 0.1 | 0.1 | 0.1 Nega- |
| CD34 (PE) | 73 | 0.7 | 0.2 | 0.4 | 0.3 | 4.9 tives |
| CD45 (PE) | 0.5 | 0.1 | 0.1 | 0.1 | 0.1 | 0.1 |
| CD11b (PE) | 0.3 | 0 | 0 | 0 | 0 | 0 |
| CD19 (PE) | 0.3 | 0 | 0 | 0 | 0 | 0.1 |
| IgG1 (PE) | 0.2 | 0.2 | 0 | 0.2 | 0.1 | 0 Con- |
| IgG2a (PE) | 0.3 | 0.1 | 0 | 0.1 | 0.1 | 0.1 trols |
| IgG1 (FITC) | 0.2 | 0 | 0 | 0.1 | 0.1 | 0 |

TABLE 15

Sample 9

| Marker(dye) | Passage | | | | | |
|---|---|---|---|---|---|---|
| | 0 | 1 | 2 | 3 | 4 | 5 |
| CD73 (PE) | 99.9 | 100 | 99.9 | 100 | 99.9 | 100 Posi- |
| CD90 (PE) | 99.9 | 99.9 | 99.9 | 99.5 | 99.9 | 100 tives |
| CD105 (PE) | 99.7 | 100 | 99.7 | 99.7 | 99.9 | 99.8 |
| CD44 (FITC) | 99.8 | 99.8 | 99.8 | 99.9 | 99.8 | 99.9 |
| HLADR (PE) | 0.1 | 0 | 0.2 | 0.1 | 0.1 | 0.1 Nega- |
| CD34 (PE) | 4.1 | 2.3 | 0.1 | 3.2 | 1.2 | 2.1 tives |
| CD45 (PE) | 0.1 | 0.2 | 0 | 0.1 | 0.4 | 0.3 |
| CD11b (PE) | 0.1 | 0 | 0 | 0.1 | 0.1 | 0.1 |
| CD19 (PE) | 0.2 | 0.1 | 0.1 | 0.3 | 0.1 | 0.1 |
| IgG1 (PE) | 0.3 | 0.3 | 0.2 | 0.2 | 0.2 | 0.2 Con- |
| IgG2a (PE) | 0.2 | 0.1 | 0.2 | 0.1 | 0.1 | 0.1 trols |
| IgG1 (FITC) | 0.1 | 0.1 | 0.1 | 0.1 | 0.1 | 0.2 |

TABLE 16 average
Average

| Marker (dye) | Passage | | | | | |
|---|---|---|---|---|---|---|
| | 0 | 1 | 2 | 3 | 4 | 5 |
| CD73 (PE) | 99.8 | 99.9 | 99.9 | 99.9 | 99.9 | 100.0 Posi- |
| CD90 (PE) | 99.4 | 99.9 | 99.9 | 99.9 | 99.8 | 100.0 tives |
| CD105 (PE) | 94.0 | 90.3 | 90.4 | 94.8 | 94.5 | 96.6 |
| CD44 (FITC) | 99.5 | 99.0 | 99.4 | 99.6 | 99.7 | 99.4 |
| HLADR (PE) | 0.5 | 0.1 | 0.1 | 0.1 | 0.1 | 0.1 Nega- |
| CD34 (PE) | 19.5 | 2.7 | 2.0 | 4.4 | 3.3 | 6.1 tives |
| CD45 (PE) | 1.0 | 2.6 | 0.4 | 1.4 | 0.6 | 0.6 |
| CD11b (PE) | 0.4 | 0.1 | 0.1 | 0.0 | 0.1 | 0.1 |
| CD19 (PE) | 0.4 | 0.1 | 0.1 | 0.8 | 0.2 | 0.8 |
| IgG1 (PE) | 0.2 | 0.1 | 0.1 | 0.1 | 0.1 | 0.1 Con- |
| IgG2a (PE) | 0.3 | 0.1 | 0.1 | 0.1 | 0.1 | 0.1 trols |
| IgG1 (FITC) | 0.3 | 0.0 | 0.0 | 0.0 | 0.0 | 0.0 |

TABLE 17

StDev
StDev

| Marker (dye) | Passage | | | | | |
|---|---|---|---|---|---|---|
| | 0 | 1 | 2 | 3 | 4 | 5 |
| CD73 (PE) | 0.3 | 0.2 | 0.1 | 0.1 | 0.1 | 0.1 Posi- |
| CD90 (PE) | 1.1 | 0.1 | 0.1 | 0.2 | 0.3 | 0.0 tives |
| CD105 (PE) | 7.1 | 14.4 | 22.9 | 8.3 | 9.5 | 4.9 |
| CD44 (FITC) | 0.4 | 1.8 | 0.9 | 0.3 | 0.2 | 1.3 |
| HLADR (PE) | 0.4 | 0.1 | 0.1 | 0.1 | 0.1 | 0.1 Nega- |
| CD34 (PE) | 22.6 | 3.2 | 3.2 | 7.3 | 2.2 | 5.6 tives |
| CD45 (PE) | 1.1 | 6.7 | 0.7 | 3.1 | 0.7 | 0.7 |
| CD11b (PE) | 0.5 | 0.1 | 0.3 | 0.1 | 0.1 | 0.2 |
| CD19 (PE) | 0.3 | 0.1 | 0.1 | 1.9 | 0.2 | 1.2 |
| IgG1 (PE) | 0.1 | 0.1 | 0.1 | 0.1 | 0.1 | 0.1 Con- |
| IgG2a (PE) | 0.1 | 0.1 | 0.1 | 0.1 | 0.1 | 0.1 trols |
| IgG1 (FITC) | 0.3 | 0.0 | 0.1 | 0.1 | 0.1 | 0.1 |

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method of treating multiple sclerosis comprising administering to a subject in need thereof a synergistic combination of (i) a pharmaceutical composition comprising glatiramer acetate, the pharmaceutical composition being in a sustained release depot form administered parenterally, and (ii) human adipose-derived stem cells (hADSCs) administered into the central nervous system (CNS) of the subject, wherein the hADSCs are isolated hADSCs sub-cultured to a passage number between 3-10 passages.

2. The method of claim 1, wherein the pharmaceutical composition comprising glatiramer acetate is administered once every 1-6 weeks or once every 4 weeks.

3. The method of claim 1, wherein the pharmaceutical composition comprising glatiramer acetate is formulated for intramuscular administration, and the administering is via intramuscular injection.

4. The method of claim 1, wherein the pharmaceutical composition comprising glatiramer acetate is formulated for subcutaneous implantation, and the administering is via subcutaneous injection.

5. The method of claim 1, wherein administering the hADSCs is by intrathecal, intraventricular or intracerebroventricular (ICV) administration.

6. The method of claim 1, wherein the hADSCs are autologous.

7. The method of claim 1, wherein the hADSCs are allogeneic.

8. The method of claim 1, wherein the hADSCs are characterized by positive expression of CD44, CD73 and CD90 by at least 95% of the cells, positive expression of CD105 by at least 90% of the cells, and negative expression of CD45, CD19, CD11B and HLADR by at least 95% of the cells.

9. The method of claim 8, wherein the hADSCs are further characterized by positive expression of CD34 by 0.1-10% of the cells.

10. The method of claim 1, wherein administering the hADSCs comprises administrating about $10^5$-$3\times10^8$ cells per one administration.

11. The method of claim 1, wherein the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

12. The method of claim 1, wherein the glatiramer acetate comprises about 15 to about 100 amino acids.

13. The method of claim 1, wherein the pharmaceutical composition comprising glatiramer acetate comprises a pharmaceutically acceptable biodegradable or non-biodegradable carrier of glatiramer acetate.

14. The method of claim 13, wherein the carrier is selected from the group consisting of poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, gelatin, collagen, oxidized cellulose, and polyphosphazene.

15. The method of claim 1, wherein the pharmaceutical composition comprising glatiramer acetate is in the form of microparticles prepared by a water-in oil-in water double emulsification process.

16. The method of claim 15, wherein the microparticles comprise an internal aqueous phase comprising a therapeutically effective amount of glatiramer acetate, a water immiscible polymeric phase comprising a carrier selected from a biodegradable and a non-biodegradable polymer, and an external aqueous phase.

17. The method of claim 16, wherein the water immiscible polymeric phase comprises a biodegradable polymer selected from PLA and PLGA.

18. The method of claim 16, wherein the external aqueous phase comprises a surfactant selected from polyvinyl alcohol (PVA), polysorbate, polyethylene oxide-polypropylene oxide block copolymers and cellulose esters.

19. The method of claim 1, wherein the pharmaceutical composition comprising glatiramer acetate comprises between about 20-500 mg of glatiramer acetate.

20. The method of claim 1, wherein the subject is suffering from a progressive form of multiple sclerosis.

21. The method of claim 1, wherein the hADSCs are isolated hADSCs sub-cultured to a passage number between 4-5 passages.

* * * * *